United States Patent [19]

Stenglein et al.

[11] Patent Number: 5,051,361

[45] Date of Patent: Sep. 24, 1991

[54] AZT IMMUNOASSAYS, DERIVATIVES, CONJUGATES AND ANTIBODIES

[75] Inventors: Kenneth J. Stenglein, St. Louis; Dennis M. Murray, Eureka, both of Mo.

[73] Assignee: Sigma Chemical Company, St. Louis, Mo.

[21] Appl. No.: 259,872

[22] Filed: Oct. 19, 1988

[51] Int. Cl.[5] .................. G01N 33/533; G01N 33/535
[52] U.S. Cl. .................... 435/7.9; 435/7.92; 435/7.93; 435/21; 435/28; 435/70.21; 435/125; 435/172.2; 435/240.27; 436/543; 436/544; 436/546; 436/548; 530/387; 530/408; 530/807; 935/103; 935/110
[58] Field of Search .................. 435/7, 21, 28, 6, 125, 435/70.21, 808, 172.2, 240.27, 7.9, 7.92, 7.93; 436/528, 543, 544, 546, 548; 530/807, 387; 424/7.1, 85.8; 935/89, 103, 110

[56] References Cited

U.S. PATENT DOCUMENTS

| 4,724,232 | 2/1988 | Rideout et al. | 514/50 |
| 4,824,941 | 4/1989 | Gordon et al. | 436/548 |

FOREIGN PATENT DOCUMENTS

| 0217580 | 9/1986 | European Pat. Off. | 19/73 |
| 0253517 | 6/1987 | European Pat. Off. | 31/70 |

OTHER PUBLICATIONS

Blum, M. Robert, Ph.D. et al., "Pharmacokinetics and Bioavailability of Zidovudine in Humans", The American Journal of Medicine, vol. 85 (suppl 2A), Aug. 29, 1988, pp. 189–194.
Furman, Phillip A. et al., "Phosphorylation of 3'-Azido-3'-Deoxythymidine and Selective Interaction of the 5'-Triphosphate with Human Immunodeficiency Virus* Reverse Transcriptase", Proceedings of the National Academy of Sciences, U.S.A., vol. 83, Nov. 1986, pp. 8333–8337.
Glinski, Ronald P. et al., "The Synthesis of Phosphorylated 3'-Amino-3'-Deoxythymidine and 5'-Amino-5'-Deoxythymidine", Chemical Communications, 1970, pp. 915–916.
Glinski, Ronald P. et al., "Nucleotide Synthesis. IV.[1] Phosphorylated 3'-Amino-3'-Deoxythymidine and 5'-Amino-5'-Deoxythymidine and Derivatives[2,3]", J. Org. Chem., vol. 38, No. 25, 1973, pp. 4299–4305.
Good, S. S. et al., "Biotransformation in Various Species and in Humans of 3'-Azido-3'-Deoxythymidine, A Potential Agent for the Treatment of Aids", Abstract No. 1690, Federation Proceedings, Federation of American Societies for Experimental Biology, vol. 45, No. 3, Mar. 1, 1986, p. 444.
Good, Steven S. et al., "Simultaneous Quantification of Zidovudine and Its Glucuronide in Serum by High-Performance Liquid Chromatography", Journal of Chromatography, 431 (1988), pp. 123–133.
Henry, Keith, M. D. et al., "Concurrent Zidovudine Levels in Semen and Serum Determined by Radioimmunoassay in Patients with Aids or Aids-Related Complex", JAMA, vol. 259, No. 20, May 27, 1988, pp. 3023–3026.
Horwitz, Jerome P. et al., "Nucleosides, V. The Monomesylates of 1-(2'-Deoxy-β-D-Lyxofuranosyl)-Thymine[1,2]," Journal of Organic Chemistry, vol. 29, Jul., 1964, pp. 2076–2078.
Imazawa, M. and F. Eckstein, "Synthesis of 3'-Azido-2',3'-Dideoxyribofuranosylpurines", Journal of Organic Chemistry, vol. 43, No. 15, 1978, pp. 3044–3048.
Incstar Corporation, "ZDV-TRAC TM RIA: AZT, Retrovir, Zidovudine", Incstar Science Technology and Research, Package Insert, Part #11688, Revised Jun. 1988.
Krasny, H. C. and S. S. Good, "Pharmacokinetics and Metabolism of Azidothymidine in the Dog", Abstract No. 311, Federation Proceedings, Federation of American Societies for Experimental Biology, vol. 45, No. 3, Mar. 1, 1986, p. 207.
Krodstad, D. J. et al., "Fluorescence Polarization Immunoassay for AZT", Abstract No. 1464, Program and Abstracts of the Twenty-Eight Interscience Conference on Antimicrobial Agents and Chemotherapy, ASM News, vol. 54, No. 8, 1988, p. 371.
Krodstad, D. J. et al., "Fluorescence Polarization Immunoassay for Azidothymidine", ASM News (American Society for Microbiology), vol. 54, No. 8, Aug., 1988, No. 1464.
Matsuda, Akira et al., "Nucleosides. 115. Reaction of 3'-O-Mesythymidine. Formation of 1-(3-Azido-2,3—Dideoxy-β-D-Threo-Pentofuranosyl)Thymine and Its Conversion into 6,3'-Imino-1-(2,3-Dideoxy-β-D-Threo-Pentofuranosyl)Thymine[1]," Journal of Organic Chemistry, vol. 45, No. 16, 1980, pp. 3274–3278.
Quinn, Richard P. et al., "A Radioimmunoassay for Azidothymidine (AZT) Using a High Specific Activity Tritiated Antigen", Abstract No. 1465, Program and Abstracts of the Twenty-Eighth Interscience Conferene on Antimicrobial Agents and Chemotherapy, ASM News, vol. 54, No. 8, 1988, p. 371.
Quinn, R. P. et al., "Radioimmunoassay for Azidothymidine Using a High-Specific-Activity Tritiated Antigen", Program No. 1465, 1988 ICAAC Program, ASM News, vol. 54, No. 8, 1988.

*Primary Examiner*—Mary E. Ceperley
*Attorney, Agent, or Firm*—Senniger, Powers, Leavitt & Roedel

[57] ABSTRACT

This invention relates to a method for the immunoassay of AZT (3'-azido-3'-deoxythymidine), also known as zidovudine, in biological fluids such as serum, semen, plasma and urine, as well as other body fluids. The invention also includes (1) various novel analogs of AZT useful in preparing immunogens for antibodies to AZT and in preparing labeled AZT, (2) immunogens for antibodies to AZT, (3) monoclonal and polylonal antibodies to AZT, (4) labeled AZT analogs and (5) diagnostic test kits for the immunoassay.

20 Claims, No Drawings

AZT IMMUNOASSAYS, DERIVATIVES, CONJUGATES AND ANTIBODIES

This invention relates to a method for the immunoassay of AZT (3'-azido-3'-deoxythymidine), also known as zidovudine, in biological fluids such as serum, semen, plasma and urine, as well as other body fluids. The invention also includes (1) various novel analogs of AZT useful in preparing immunogens for antibodies to AZT and in preparing labeled AZT, (2) immunogens for antibodies to AZT, (3) monoclonal and polyclonal antibodies to AZT, (4) labeled AZT analogs and (5) diagnostic test kits for the immunoassay.

BACKGROUND OF THE INVENTION

Competitive binding immunoassays for quantitatively measuring the presence of physiologically active compounds (ligands) are based on the competition between a ligand in a test sample and a labeled reagent, referred to as a tracer, for a limited number of binding sites on antibodies or receptors specific to the ligand and the tracer. The concentration of ligand in a sample to be assayed determines the amount of tracer or label that will specifically bind to an antibody. By measuring the amount of tracer-antibody complex a quantitative determination of the amount of ligand in the test sample is provided.

When necessary, modification of such ligand to prepare an immunogen should take into account the effect on the structural specificity of the antibody. That is, in choosing a site on a ligand for conjugation to a carrier such as protein, the selected site is chosen so that administration of the resulting immunogen will provide antibodies which will recognize the original ligand. Furthermore, not only must the antibody recognize the original ligand, but significant characteristics of the ligand portion of the immunogen must remain so that the antibody produced after administration of the immunogen will more likely distinguish compounds closely related to the ligand which may also be present in the patient sample. In addition, the antibodies should have high binding constants.

Also, the tracer must effectively compete with the ligand for antibody binding in a reproducible manner and provide for significant changes in the measured signal with small changes in the concentration of the ligand over the concentration range of interest.

Other considerations for an immunoassay method are that it is not affected by materials present in the sample to be assayed, an easily determinable signal is obtained, the tracer, standards and antibodies have good storage life and are stable under the assay conditions. Also, the tracer and standards must be readily recognizable by the antibodies for the ligand.

AZT (3'-azido-3'-deoxythymidine) which can be represented by the formula:

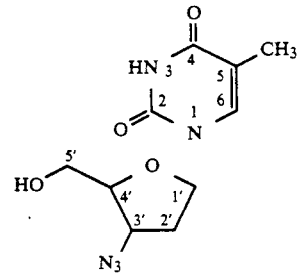

has been shown to be an effective drug in the treatment of Acquired Immunodeficiency Syndrome (AIDS). As with any drug, and especially one having serious side effects at high dosage levels, such as AZT, the formal establishment of a therapeutic range for a patient being treated with the drug is necessary. The recognized method for measuring AZT plasma levels employs high performance liquid chromatography (HPLC) which is a sensitive and reasonably precise technique. However, although HPLC can be used for measuring AZT concentrations in noninfective samples and in HIV-positive samples, the HPLC method is not practical for the routine monitoring of AZT in HIV-positive samples due to the disadvantages of a long analysis time, elaborate sample preparation requirements, including complicated solid phase extraction, a relatively large sample size (500 ul), and interference by body fluid components in the sample. A particular problem in using HPLC to monitor AZT levels in pediatric patients is the difficulty in obtaining samples of sufficient volume. Also, HPLC is especially subject to interference from endogenous compounds in patients with renal failure.

The development of an analytical method for measuring AZT levels in a patient being treated with AZT which could minimize sample manipulation, employ disposable equipment as much as possible, reduce the sample size needed and shorten the length of the assay time is therefore needed. It is preferred that such a method not be subject to interference from endogenous compounds, (e.g. in patients with renal disease) or hemolysis or typically prescribed drugs.

SUMMARY OF THE INVENTION

Immunoassays provide a useful method for quantitatively determining drug levels in small samples (1–250 ul), have a rapid turn-around time, are easy to perform and can be automated for processing large numbers of samples. Immunoassays are therefore suitable for measuring levels of drugs in patients and are especially useful where sample handling must be minimized.

It is therefore an object of this invention to provide an assay for the determination of AZT (3'-azido-3-deoxythymidine) levels in a sample which meets the needs described above, especially in the establishment of a formal therapeutic range in a patient undergoing treatment with AZT. More specifically it is an object of this invention to provide an immunoassay for determining the presence or amount of a ligand, namely AZT, in a sample. The immunoassay comprises intermixing with said sample a labeled analog of AZT (tracer) or biologically acceptable salt thereof, and an antibody capable of specifically recognizing said ligand and said tracer, and then determining the amount of tracer bound to antibody by a suitable technique.

A further object is to provide a competitive binding assay having many advantages over an HPLC assay, including the requirement of a smaller sample size, allowing for its use with pediatric patients, decreased assay time, simple extraction procedures and a lack of interference from serum components or cross-reactivity with other drugs or drug metabolites. It is recognized that noncompetitive immunoassays are possible and is contemplated that the AZT antibodies within the scope of the invention would be useful for the determination of AZT concentration using such immunoassays. Further, the application of such AZT antibodies to such immunoassays is within the skill of the art.

A still further object is to provide various novel materials useful in carrying out the method of this invention or for the preparation of such materials including (1) analogs of AZT which are suitable for preparing immunogens for AZT by coupling to a carrier, such as protein, or, are suitable for preparing labeled AZT derivatives (tracers) by coupling to indicator moieties, such as fluorescein; (2) immunogens suitable for the preparation of monoclonal or polyclonal antibodies to AZT; (3) antibodies obtained from the immunization of suitable animal species with such immunogens; and (4) labeled AZT derivatives suitable for use in the method of this invention.

In addition, an object of the invention is to Provide a diagnostic kit useful in the practice of the immunoassays of the invention.

It is also contemplated that compounds similar in structure to AZT will be developed for the treatment of AIDS, and a further object of this invention therefore is to provide an assay for those AZT-related compounds to the extent that such compounds are recognized by antibodies to AZT.

These and other objects will become apparent from the detailed description of the invention.

DETAILED DESCRIPTION OF THE INVENTION

For any immunoassay method there are three essential ingredients: a tracer, an antibody, and the sample to be analyzed. Of course standards, containing known amounts of ligand are also necessary in order to provide a basis for the determination of the ligand level in the sample to be analyzed. Controls may also be utilized to verify the accuracy of the analysis.

AZT Immunoassay

In accordance with the method of this invention a sample containing or suspected of containing AZT is intermixed with a tracer or a biologically acceptable salt thereof and an antibody specific to AZT and the tracer. AZT present in the sample and the tracer compete for a limited number of antibody binding sites resulting in the formation of AZT-antibody and tracer-antibody complexes. By maintaining the concentration of tracer and antibody constant, the amount of tracer-antibody complex formed is inversely proportional to the amount of AZT present (as AZT-antibody complex) in the sample. By determining the amount of tracer-antibody complex in the reaction mixture a quantitative determination of the amount of AZT in the sample is made.

The concentration of AZT in the sample assayed will vary depending on the establishment of a therapeutic dosage based upon, for example, the body fluid measured and dose given. The sensitivity of the assay may be optimized accordingly. High concentrations of AZT may be assayed by dilution of the original sample.

In addition to the concentration range of AZT, considerations such as whether the assay is qualitative, semiquantitative or quantitative, the equipment employed, and the characteristics of the tracer and antibody will normally determine the concentration of the tracer and antibody to be employed. While the concentration of AZT in the sample will normally determine the range of concentration of the tracer and the antibody, in order to optimize the sensitivity of the assay, individual concentrations of tracer and antibody will be determined empirically. The latter concentrations can be readily ascertained by those skilled in the art. Other considerations involved in optimizing a particular immunoassay include PH and assay temperature.

The pH at which the method of the present invention is practiced should be controlled in those assays where pH is important, for example assays using a fluorescein derivative. Various buffers may be employed in order to achieve and maintain the desired pH during the assay procedure. Representative buffers include borate, phosphate, carbonate, tris(hydroxymethyl)aminomethane (Tris), barbital, and the like. The particular buffer selected is not critical for the present invention, but in an individual assay, a specific buffer may be preferred in view of the method chosen and the components employed. The cation portion of the buffer will generally determine the cation portion of the tracer salt in solution.

The methods of the present invention are practiced at moderate temperatures and preferably at a constant temperature. The temperature will normally range from about 0° C. to about 50° C., more typically from about 15° C. to about 40° C.

The invention is not limited to a particular assay procedure, and therefore is intended to include both homogeneous and heterogeneous procedures, including procedures such as fluorescence polarization immunoassay (FPIA), fluorescence immunoassay (FIA), enzyme immunoassay (EIA), nephelometric inhibition immunoassay (NIA), and radioimmunoassay (RIA). The indicator moiety is selected so as to meet the needs of various users of the method which are often dictated by the availability of assay equipment and compatible immunoassay procedures.

Homogeneous immunoassays are assays that do not require the separation of antibody bound tracer from free tracer. The antigen-antibody interaction causes, directly or indirectly, a measurable change in the signal.

The preferred homogeneous assays are those utilizing an enzyme or a fluorescent reagent, because they are nonisotopic, resulting in fewer waste disposal problems. Enzyme immunoassays are also preferred because they are quite sensitive and are therefore capable of measuring a lower AZT concentration. Both of these types of assays are also precise and easily automated, the assays are simple, the sample size per assay is relatively small, and assay results compare well with results obtained from an HPLC assay.

A preferred homogeneous immunoassay is a fluorescence polarization immunoassay (FPIA). For example, one can use fluorescein labeled AZT as the tracer. Briefly, fluorescein labeled AZT and unlabeled AZT present in the sample to be analyzed compete for a limited number of antibody combining sites. Increasing amounts of unlabeled AZT present in a given sample leads to a corresponding decrease in the amount of antibody bound fluorescein labeled AZT and causes a decrease in the polarization of the sample. The extent of polarization is therefore inversely proportional to the AZT concentration in the sample. See for example, Dandliker, W. B. and de Saussure V. A., *Immunochemistry*, 7, 799 (1970).

A protein precipitating reagent may be necessary in fluorescence immunoassays including fluorescence polarization immunoassays. The precipitating reagent is used to gain sensitivity by reducing nonspecific background fluorescence and scattering of light due to various materials present such as serum proteins and bilirubin -albumin complexes. The present invention includes the addition, to the sample to be analyzed, of a precipitating reagent such as trichloroacetic acid, with or without methanol; sulfosalicylic acid, with methanol, or dioxane or N,N-dimethylacetamide; polyvinyl sulfonic acid with or without methanol as well as with sulfuric acid or phosphoric acid, and chromotropic acid with methanol. After precipitation of a portion of the interfering compounds and their separation, the PH of the serum extract (supernatant) should be adjusted by using a buffer with sufficient buffering capacity to permit the ligand-antibody interaction to occur under favorable conditions. Examples of such buffers are: glycine; phosphate; borate; carbonate; Tris; ethanolamine; triethanolamine; diethanolamine; piperazine; tricine; and ammonia. In the present invention, the preferred buffer is a Tris base solution.

Substrate-labeled fluorescent immunoassay is another homogeneous immunoassay in which an enzyme, such as $\beta$-galactosidase hydrolyzes a non-fluorescent conjugate of AZT, such as AZT-umbelliferone-$\beta$-galactoside, producing a fluorescent product which can be measured in a spectrofluorometer. Since the antibody to AZT will bind to the non-fluorescent AZT conjugate and interfere with the conversion of the conjugate to the fluorescent product, the addition of AZT creates a competition for AZT antibody combining sites. Thus, the concentration of fluorescent product is proportional to the concentration of AZT.

Fluorescence quenching and fluorescence enhancement immunoassays are other homogeneous fluorescent assays based on the observation that some antibodies, upon binding to a fluorescent molecule, cause either an enhancement or decrease in fluorescence. For example, AZT can be conjugated to a fluorescent molecule which, upon binding to selected AZT antibodies will quench the fluorescence of the fluorescent AZT conjugate. AZT will compete with the fluorescent AZT conjugate for a limited number of AZT antibody combining sites and reduce the amount of quenching. Therefore, the fluorescence intensity of the assay is proportional to the AZT concentration.

A homogeneous immunoassay using phosphorescence quenching of erythrosin can be performed in a manner similar to that used in fluorescence quenching.

Enzyme immunoassays (EIA) are a broad class of immunoassays based upon the determination of enzyme activity as a measure of the antigen-antibody interaction. Homogeneous enzyme immunoassays are assays that do not require the separation of the bound tracer from free tracer, but rely on modulation of enzyme activity by the specific interaction of antigen with antibody.

For example, AZT can be conjugated near the active site of an enzyme such as glucose-6-phosphate dehydrogenase. Upon the addition of antibodies to AZT, the subsequent enzyme activity is reduced by steric interference of the antibody with the enzyme substrate. The addition of AZT competes with the AZT-enzyme conjugate for a limited number of antibody combining sites, thus preventing interference by antibodies to AZT with enzyme activity. The enzyme activity is directly proportional to the AZT in the sample.

Cofactor-labeled antigen EIA is yet another type of homogeneous enzyme immunoassay that can be performed by conjugating AZT to a cofactor. One such cofactor is nicotinamide-6-(2-amino-ethylamino) adenine dinucleotide (aeaNAD+). The addition of antibodies to AZT binds the AZT-aeaNAD+ conjugate and inhibits the activity of an NAD dependent enzyme, such as lactate dehydrogenase. AZT will compete with AZT-aeaNAD+ for a limited number of AZT antibody combining sites. As a result a change in absorbance of the reaction mixture will be proportional to the AZT concentration.

An additional type of homogeneous immunoassay is an agglutination immunoassay (AIA). For example, latex particles can be coated with a multivalent AZT conjugate (prepared by conjugating AZT analogs to a carrier) and will agglutinate (clump) upon addition of antibodies to AZT. The addition of AZT will cause competition for the limited number of antibody combining sites and cause a decrease in the turbidity of the mixture. Erythrocytes have also been used as indicator particles in place of latex particles.

A nephelometric inhibition immunoassay (NIA) is another type of homogeneous immunoassay that utilizes a multivalent AZT conjugate. Typically this conjugate is prepared from a high molecular weight carrier such as horse apoferritin or serum proteins. Upon addition of antibody to AZT, the multivalent AZT conjugate forms complexes with the antibody to AZT, thus increasing the amount of light scatter in the reaction mixture. The addition of AZT decreases the size of the complexes formed by multivalent AZT conjugates and antibodies to AZT, by competing with the multivalent AZT conjugate for a limited number of antibody combining sites.

A sol particle immunoassay (SPIA) utilizes inorganic colloidal particles as the tracer. While SPIA can be performed as a heterogeneous immunoassay, it can also be structured as a homogeneous immunoassay. For example, in a gold SPIA antibodies to AZT can be adsorbed to gold particles. The addition of multivalent AZT conjugates causes the gold-antibody to AZT complexes to agglutinate causing a change in the absorption spectrum of the gold particles, i.e., the color changes from red to blue. AZT will compete with the multivalent AZT conjugates, decreasing the color change.

Heterogeneous immunoassays are assays that require the separation of bound tracer from free tracer prior to determining the amount of ligand in the sample. While homogeneous immunoassays are most preferred because they do not require the additional separation step of heterogeneous immunoassays, among heterogeneous immunoassays those with a radioactive or enzyme group as the indicator group are preferred. This is because, like homogeneous EIAs, radioactive or enzymatic heterogeneous immunoassays are precise, easily automated, utilize a small sample size and can be more sensitive than FPIAs.

Radioimmunoassays (RIA) are heterogeneous immunoassays utilizing radioactively labeled ligands. For example, AZT can be directly labeled with $^3$H or an AZT analog can be labeled with $^{125}I$. Labeled AZT competes with unlabeled AZT for a limited number of antibody combining sites. After the bound complex of labeled AZT-antibody to AZT is separated from the unbound (free) labeled AZT, the radioactivity in the bound fraction, or free fraction or both is determined in an appropriate radiation counter. The concentration of bound labeled AZT is inversely proportional to the concentration of unlabeled AZT. The antibody to AZT can be in solution with separation of free and bound AZT being accomplished using charcoal or a second antibody specific for the animal species whose immunoglobulin contains the antibody to AZT. Alternatively, antibody to AZT can be attached to the surface of an insoluble material. In this case, separation of bound and free AZT is performed by appropriate washing.

Immunoradiometric assays (IRMA) generally refer to heterogeneous immunoassays in which the antibody reagent is radioactively labeled (the tracer). An IRMA requires the production of a multivalent AZT conjugate, as for example by conjugation to a protein such as rabbit serum albumin. The multivalent AZT conjugate must have at least 2 AZT residues per molecule and the AZT residues must be of sufficient distance apart to prevent steric interference of binding by at least two antibodies to AZT. For example, in an IRMA the multivalent AZT conjugate can be attached to a solid surface such as a plastic sphere. Unlabeled AZT and antibody to AZT which is radioactively labeled are added to a test tube containing the multivalent AZT conjugate coated sphere. The AZT competes with the multivalent AZT conjugate for AZT antibody binding sites. After an appropriate time, the unbound reactants are removed by washing and the amount of radioactivity on the solid phase is determined. The radioactivity bound is inversely proportional to the concentration of AZT.

Alternatively, antibody to AZT can be used to coat the plastic sphere. The addition of the multivalent AZT conjugate and AZT results in a competition for binding sites on the solid phase antibody sphere. After an appropriate incubation, the sphere is washed and an excess of radioactively labeled antibody to AZT is added. The sphere is again washed after an appropriate incubation and the radioactivity bound to the sphere is determined. The amount of radioactivity is inversely proportional to the AZT concentration.

Another preferred heterogeneous immunoassay involves the use of enzyme labels such as horseradish peroxidase, alkaline phosphatase, and $\beta$-galactosidase. The heterogeneous EIA differs from the homogeneous EIA in that determination of the amount of ligand in the sample requires a separation of bound from free tracer not required in the homogeneous EIA. For example, AZT labeled horseradish peroxidase competes with unlabeled AZT for a limited number of antibody combining sites present on antibodies to AZT attached to a solid surface such as a microtiter plate. The AZT antibodies may be attached to the microtiter plate directly after fractionating antiserum containing AZT antibodies with ammonium sulfate or indirectly by first coating the microtiter plate with multivalent AZT conjugates (coating antigens) prepared for example by conjugating AZT with serum proteins such as rabbit serum albumin (RSA). After separation of the bound labeled AZT from the unbound labeled AZT, the enzyme activity in the bound fraction is determined spectrophotometrically at a fixed period of time after the addition of substrate.

The above examples of preferred heterogeneous immunoassays describe the use of radioactively and enzymatically labeled tracers. Alternatively, assays other than EIA that exploit nonisotopic detection systems have been described. These labels include fluorescent materials such as fluorescein, 5-dimethylaminonaphthalene-1-sulfonyl derivatives and rhodamine; phosphorescent materials such as erythrosin and europium; luminescent materials such as luminol and luciferin; and sols such as gold and organic dyes.

Variations to the above described assay designs will be obvious to those skilled in the art.

AZT Compounds

According to this invention, novel derivatives of AZT have been developed for use in the competitive binding assays of this invention as well as for the preparation of such derivatives which can be represented by the general formula:

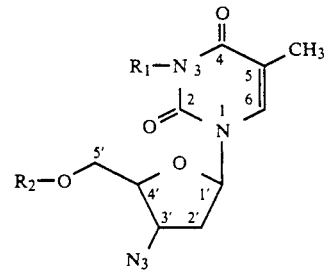

where $R_1$ and $R_2$ are selected from hydrogen and R-A, provided that one of $R_1$ and $R_2$ is hydrogen, R is a linking group, and A is L, X or Y, where L is a leaving group, X is an indicating moiety and Y is a carrier.

AZT Linking Groups

The AZT linking group (spacer) represented by R can be a group of from 0 to 50 atoms other than hydrogen although even larger spacers could be effectively utilized in preparing AZT derivatives by attaching an AZT analog to groups such as oligopeptides, polyamino acids, polymers, carbohydrates and/or cyclic groups as well as by glutaraldehyde copolymerization of aminated AZT analogs with polyamino acids. The atoms comprising R can include from 0 to 30 carbon atoms and from 0–25 hetero atoms selected from oxygen, nitrogen, sulfur and halogen. Generally the atoms of R are present in functional groups as for example alkyl, carbonyl, nonoxocarbonyl, hydroxy, alkoxy, amido, halo, thiocarbonyl, cyano, nitrilo, thio, imino, amino, carbalkoxy, mercuri, phthalimido, formyl, keto, succinimidoxy, thiocarbamyl, azo, hydroxyphenyl, and imidazolyl, as well as other saturated or unsaturated carbocyclic or heterocyclic rings. Preferably R can be from 0 to 30 atoms other than hydrogen including 0 to 20 carbons and 0–10 hetero atoms. More preferably R can be from 1 to 23 atoms other than hydrogen including 1 to 16 carbons and 0–7 hetero atoms. It is even more preferred that R is succindioyl, aminoalkyl or of the structure $-(CH_2)_n-CO-$ or $-(CH_2)_n-NH-$ or $-CO-(CH_2)_n-CO-$, where n is a whole number from 1 to 19, preferably 1 to 8. Even more preferred compositions of R are discussed below with respect to the various groups represented by A. For convenience, the representation AZT as well as other shorthand designations of various AZT substituents is often used herein in naming various compounds instead of the commonly accepted chemical nomenclature. For example, 3'-azido-3'-deoxythymidyl-5'-hemisuccinate can be referred to as AZT-5'-hemisuccinate or simply AZT-5'-HS.

In the case of multivalent AZT conjugates (test or coating antigen) used for example in EIAs and NIAs as well as for immunogens and AZT-R-enzyme derivatives it would be expected to be somewhat easier to make them using linking groups R having 1 to 35 atoms comprising 1 to 25 carbon atoms and 0 to 10 hetero atoms. The preferred embodiments for R include up to 7 atoms comprising up to 6 carbon atoms and up to 2 hetero atoms. Illustrative examples of preferred embodiments include:

| Example No. | (AZT-position)-R:(A) | R (No. of Atoms) Total (Other than H) | Carbon | Hetero |
|---|---|---|---|---|
| 4 | (AZT-3)-(CH$_2$)$_4$—CO:(BSA) | 6 | 5 | 1 |
| 9 | (AZT-3)-(CH$_2$)$_4$—CO:(HRPO) | 6 | 5 | 1 |
| 44 | (AZT-5')-CO—(CH$_2$)$_2$—CO:(APO) | 6 | 4 | 2 |

In the case of fluorescent derivatives it should be kept in mind that while, as in the case with the other derivatives, there is a theoretical limit to the size of R, when a fluorescent derivative is used in an FPIA, that fluorescent derivative should have a molecular weight less than approximately 60,000. Otherwise, free versus bound fluorescent tracer is difficult to distinguish by FPIA. Easier preparation of satisfactory fluorescent derivatives would be expected when the linking group R is up to 48 atoms comprising up to 24 carbon atoms and up to 24 hetero atoms. Good performance has been observed for fluorescent derivatives having R groups of up to 14 atoms comprising up to 8 carbon atoms and up to 6 hetero atoms. The preferred embodiments of fluorescent derivatives have up to 8 atoms comprising up to 5 carbon atoms and up to 3 hetero atoms. Examples of such preferred fluorescent derivatives include:

| Example No. | (AZT-position)-R:(A) | R (No. of Atoms) Total (Other than H) | Carbon | Hetero |
|---|---|---|---|---|
| 13 | (AZT-3)-(CH$_2$)$_3$—CO—NH: (Fluorescein Isomer I) | 6 | 4 | 2 |
| 30 | (AZT-3)-(CH$_2$)$_3$—NH—CS—NH: (Fluorescein) | 7 | 4 | 3 |

It is also contemplated that the tracer could be radioactive. In that case, it is expected that the preferred linking group R could be up to 40 atoms, of which there could be up to 30 carbon and up to 15 hetero atoms. With radioactive AZT tracers it should be noted that when using $^3$H as the indicating group, $^3$H can be substituted directly into AZT or any AZT analog as well as being attached to another compound that is subsequently attached to AZT.

Attachment of R to the hapten (AZT) can occur at any one of several available sites in the AZT molecule. Generally, the most satisfactory tracers are obtained when R is attached at the same position of the hapten molecule to which the linking group was attached when preparing the immunogen. Furthermore, the linking group R can be the same for the tracer and the immunogen (homologous linking groups). For example, tracers for RIAs are frequently prepared from the same haptenic analog used for preparing the immunogen. Hence, R will be the same in both cases. There are instances, however, in which a different linking group will be needed in the tracer than was used in the immunogen (heterologous linking groups) in order to provide an acceptable assay. One reason is that when the linking group is identical in both the tracer and immunogen (homologous linking groups) the resulting antibodies tend to show a significantly greater affinity for the tracer than for the native or underivatized hapten (i.e., the analyte), thus reducing the ability of the analyte to compete effectively with the tracer in an assay, resulting in loss of assay sensitivity. The need for heterologous linking groups is especially pronounced for tracers intended for FPIAs since small variations in R have a great effect on the tracer-antibody binding properties in an FPIA.

The selection of a heterologous linking group is a complex problem involving many considerations including:

1. The functional group in the hapten (AZT) or in the leaving group (L) or indicator moiety (X) or carrier (Y), to be modified;
2. Composition of the linking group in the immunogen;
3. Method of attaching the linking group (R) to AZT and either L or X or Y which may necessitate modifying AZT and/or L or X or Y prior to linkage so that R of the final product may be comprised in whole or in part of these modifications;
4. Composition of the linking group being considered including length, nature (aliphatic, carbocyclic, aromatic, heterocyclic), hetero atoms and other functional groups present;
5. Availability of starting materials;
6. Means for isolating, purifying and characterizing the haptenic analog or derivative;
7. Assay protocol; and
8. Quantity and binding properties of the antibody available.

Therefore, it is often advantageous to prepare a number of possible tracers having linking groups of varying composition (see item 4 above) and select the one providing the most desirable standard curve for a given method and antibody.

Leaving Group

A leaving group is one or more atoms that is given up by a compound during the reaction of that compound with another chemical. In the case of the present invention, a leaving group is given up in the synthesis of analogs (from other analogs or AZT) and derivatives, such as immunogens and tracers.

The leaving group, L, can be hydrogen, hydroxy, halo, sulfonyloxy, or a group containing 1-8 carbons selected from, but not limited to, the moieties alkyl, alkoxy, acyl, carbobenzoxy, or succinimidoxy. It can also, for example, include a phthalimido group that decomposes as it leaves, as shown in the following reaction schemes:

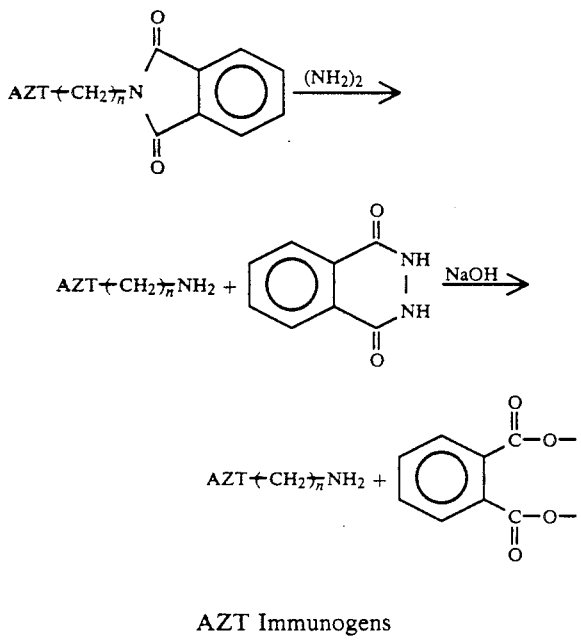

AZT Immunogens

A basic requirement common to all immunoassay methods is an antibody raised to the ligand or a closely related ligand analog. Since AZT (hapten) is a ligand that is unlikely to be immunogenic per se, it is converted to an analog, as described above, and subsequently conjugated to a carrier which is immunogenic in animals. Preferably, the carrier will be a protein type including albumins, serum proteins, e.g., globulins and lipoproteins. Illustrative proteins include bovine serum albumin, keyhole limpet hemocyanin, egg ovalbumin and bovine gamma-globulins. Synthetic polyamino acids may also be used provided they have a sufficient number of suitable groups. These conjugates can be prepared by carbodiimide mediated dehydrations as well as by many other conjugation methods. However, it is preferable when possible to prepare these conjugates by acylation of amines with active esters since a higher incorporation rate of AZT analog to carrier is likely resulting in a better immunological response to the immunogen.

Analogs or derivatives of AZT can be prepared through any one of several different positions of AZT, including the 3, 5 or 5' positions. While substitution of AZT is more easily accomplished through the 5' position, analogs or derivatives prepared through the 3 position of AZT are preferred because immunogens made from 3 position AZT analogs are more likely than immunogens made from 5' position AZT analogs to produce antibodies less cross-reactive to AZT-5'-glucuronide which is the major metabolite of AZT and is believed to be pharmacologically inactive.

Analogs containing a carboxyl function (sometimes hereinafter referred to as carboxylic acid analogs) are Preferred to analogs containing an amino function (sometimes hereinafter referred to as amino analogs) in the preparation of immunogens because the carboxylated analogs can be converted to active esters which can react with the free amino groups present in protein, assuming protein is used as the carrier. Alternatively, carboxylated AZT haptens could be coupled to proteins directly using carbodiimide (CDI) methods. In the case of carboxylic acid AZT analogs, CDI will activate the carboxyl groups on both the hapten analog and the protein which will compete for binding to the free amino groups of the protein. Similarly, in the case of amino AZT analogs, CDI will activate the carboxyl group of the protein resulting in competition between the free amino groups of the hapten and the free amino groups of the protein for binding to the activated carboxyl groups of the protein. In both cases, the use of CDI typically results in a lower incorporation rate of hapten to carrier than when a carboxylic acid active ester analog is used and activation of carboxyl groups on the protein by CDI leads to increased cross-linkage between proteins and accompanying masking of attached haptens within the cross-linked conjugates. Preferred immunogens are prepared by coupling carrier proteins to active esters of AZT formed via carboxyl bearing substituents at the 3 position of AZT.

In preparing an immunogen, the size of the hapten involved in part affects the desired length of the spacer R connecting the hapten and the carrier. For a relatively large hapten, such as digoxin, the length of the spacer is not very important since the binding sites of the antibodies produced are only able to bind a portion of the hapten. However, in the case of a relatively small hapten such as AZT, antibody binding sites would be able to bind to most of the hapten. Consequently, it is desirable to have the antibody producing cells (lymphocytes) better able to "recognize" the hapten without steric interference from the carrier. Better recognition generally results in the production of antibodies having lower cross-reactivities to compounds other than the hapten as well as having higher affinities for the hapten and thus greater assay sensitivity to the hapten.

It is contemplated, therefore, to employ immunogens preferably having a spacer of up to 7 atoms other than hydrogen to produce antibodies to AZT. More preferably the spacer for immunogens has a chain length of from four to five atoms, e.g., AZT-3-V:BSA (Example 4) and AZT-5'-S BSA (Examples 39 and 40). It is further contemplated that with a greater though still reasonable amount of optimization, operable antibodies could be produced from immunogens having a spacer having from 1 to 23 atoms other than hydrogen. It should be kept in mind that even longer spacer chain lengths could be effectively utilized in preparing immunogens by attaching AZT or an AZT analog to long length groups such as oligopeptides or to heterocyclics.

Generally, the carrier utilized in forming the immunogen is a polyamino acid which may be naturally occurring or synthetic and is usually an immunogenic polypeptide or protein. The polyamino acid may comprise constituents in addition to amino acids and will usually be of a molecular weight between about 5,000 and 5,000,000, preferably between about 15,000 and 4,000,000, and more preferably between about 30,000 and about 3,000,000. Carbohydrates, e.g., polysaccharides, liposomes, and the like can also be used. Particularly useful proteins are albumins, globulins, enzymes, hemocyanins, proteins having significant non-proteinaceous constituents, e.g., glycoproteins, and the like. Preferred examples of carrier proteins which can be used to prepare the conjugate (immunogen) are bovine serum albumin (BSA), keyhole limpet hemocyanin (KLH), and *Limulus polyphemus* hemocyanin (LPH). Albumins and globulins having a molecular weight between about 30,000 and about 200,000 are particularly preferred.

The preparation of the immunogens or conjugates can be accomplished by means known to the art. See for example, *Principles of Competitive Protein-Binding Assays, Second Edition,* Odell et al, editors, John Wiley and Sons, New York, 1983, Chapter 4, Conjugation Techniques-Chemistry, and the references discussed therein.

AZT Antibodies

The preparation of specific antibodies using the present immunogens may be accomplished by techniques known to those skilled in the art. In the usual case, a host animal such as a rabbit, goat or mouse is injected at one or more sites with an immunogen, normally emulsified with an adjuvant. Further injections are made at the same or different site or sites at regular or irregular intervals.

As is known, an animal's immune system will respond to immunization by producing antibodies that will react with one or more epitopes of the conjugate. Each plasma cell clone secretes a unique antibody (idiotype).

Monoclonal antibodies are produced in vitro by physically separating the individual plasma cell clones which have been hybridized with a tumor cell line, thus enabling one to produce antibodies of a selected idiotype for an extended period of time.

In the animal, generally multiple plasma cell clones are produced, resulting in a heterogeneous mixture of antibodies (i.e., polyclonal antibodies) in the blood.

After the blood has been collected, it will clot and the clot may be removed. The remaining liquid or serum, which contains the polyclonal antibodies may then be referred to as antiserum.

Although generally not required, purification of the antiserum may be instituted where it is found desirable to remove undesired material such as non-specific antibodies before the antiserum is considered suitable for use in performing assays.

It is to be noted that while monoclonal antibodies from a particular monoclonal line developed are identical and the polyclonal antibodies obtained from a particular animal injected are similar, variance in antibody binding properties does exist between antibodies from different monoclonal lines and/or different animals injected. Identical construction of the AZT analog portion of the tracer and of the immunogen can result in antibody binding to the tracer so great that AZT can not effectively compete with the tracer for binding to the antibody. Accordingly, when an antibody population is evaluated, a number of tracers are made in which the length and/or composition of the spacer linking the indicator moiety to AZT is varied in order to optimize the binding properties of the antibodies versus the tracer and AZT.

AZT Tracers

The preparation of the tracers of this invention from AZT analogs involves the coupling of the analog with a suitable indicator or indicator derivative. Coupling can be accomplished by means known to the art. Furthermore, from the above description of the assay of this invention it is evident that the indicator moiety is not critical to the invention and can be selected by those skilled in the art based upon the various criteria previously discussed. Tracers contemplated include those obtained by coupling an AZT analog to a fluorescent, radioactive, phosphorescent, chemiluminescent, bioluminescent, free radical or similar moiety as well as to polypeptides such as enzymes or proteins, polymers such as latex, polysaccharides such as polydextran, receptors, cofactors and enzyme inhibitors.

To prepare the tracers of this invention an analog of AZT is first prepared in such fashion that the analog has one or more antigenic determinant sites capable of binding a receptor (AZT antibody) during the course of the immunoassay. A characteristic of such AZT analog is, therefore, that it possesses sufficient structural similarity to AZT so as to be recognized by the antibody to AZT. The AZT analog may then be used to prepare the tracers of this invention as well as to prepare the immunogens used for generation of the antibodies of this invention.

Assuming a carboxylated analog is used to prepare the immunogen, then an amino analog would be one preferred for use in preparing a tracer if such analog can be prepared in reasonable yield. In general, amino analogs are more difficult to prepare than carboxylated analogs. For example, in the case where AZT-3-valeryl:BSA is the immunogen then a 3 position amino analog of AZT would be one preferred analog for use in preparing tracers. The difference in appearance between the tracer and the immunogen would serve to minimize binding of antibodies based on spacer similarity and so result in better assay sensitivity since the antibodies will be selected based on their affinity to AZT and not the spacer. In addition, this necessary selection of antibodies specific to AZT can result in the affinity of the antibodies to AZT versus the tracer being more nearly equal which is generally desirable in a competitive binding immunoassay.

Isothiocyanates, acid chlorides and active esters generally react spontaneously with amines. Furthermore, isothiocyanates of many fluorochromes are readily available. Because fluorescein isothiocyanate (FITC) derivatives are widely used in fluorescence immunoassay techniques including FPIA, a 3 position amino analog of AZT reacted with FITC is one of the preferred means of preparing such tracers as well as providing a preferred tracer. Whether FITC Isomer I, or Isomer II, or a mixture thereof, is chosen is dependent upon the particular antibodies produced and the empirical data developed with such antibodies. FITC Isomer I and Isomer II are distinguished by the fact that the isothiocyanate group is attached to the fluorescein in the 5 or 6 position, respectively. This discussion also applies to Isomers I and II of fluoresceinamine, fluoresceinamine derivatives, and erythrosin. The following structure

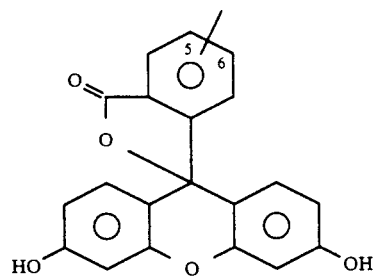

depicts the location of the 5 and 6 positions of fluorescein.

While production of an amino analog of AZT via a phthalimido AZT analog is difficult, the resulting aminoalkyl analog of AZT is stable. It also should be noted that aminopropyl AZT is prepared in better yields without the production of an immunologically inactive byproduct as is the case with aminoethyl AZT. However, it may be desirable to utilize fluorochrome derivatives other than isothiocyanates.

While FITC is a fluorescein derivative, other fluorescein derivatives as well as other fluorochromes including rhodamine derivatives and 5-dimethylaminonaphthalene-1-sulfonyl derivatives can also be used. These fluorochromes may be homogenous compounds or isomeric mixtures. Also, they may be used in their lactone form or as their biologically acceptable salts.

As used herein, the term "biologically acceptable salts" refers to salts such as the sodium, potassium, and ammonium salts, and the like, which will enable the tracers of the invention to exist in their ionized state when employed in the method of the present invention. Generally, the tracers will exist in solution as salts as a result of the buffer employed, e.g., in the presence of a sodium phosphate buffer the tracers will generally exist in their ionized state as a sodium salt.

Examples of fluorescein derivatives other than FITC which are preferred include fluoresceinthiocarbamylethylenediamine (FTED) or fluoresceinamine (FAM) or dichlorotriazinylaminofluorescein (DTAF) or methoxychlorotriazinylaminofluorescein (MTAF) or aminomethylfluorescein (AMF) or carboxyfluorescein for use in FIA or FPIA. Also, there are immunoassay techniques requiring indicator groups which may be more easily prepared by reactions other than via amino derivatives of AZT with isothiocyanates, acid chlorides, or active esters. Such indicator groups include apoferritin or rabbit serum albumin (RSA) for use in an EIA or NIA. In order to prepare tracers with such other labeling groups it is preferable to use 3 position carboxylated analogs of AZT. It is further preferred that an active ester be prepared from a carboxylated analog of AZT for subsequent reaction with the labeling group rather than activating the carboxyl group of the AZT analog with CDI for direct reaction with the labeling group. This is because in the case of labeling groups other than proteins, tracers obtained from CDI mediated reactions between the AZT analog and the labeling group would require more purification and accompanying loss of yield. In the case of proteins such as apoferritin and RSA, use of CDI would result in more cross-linkage between proteins and corresponding masking of the attached hapten (AZT) within the cross-linked conjugate so that less of the hapten is available for use in the immunoassay.

Specifically, in terms of FTED derivatives, an active ester can be used to prepare, for example, AZT-3-A:FTED (Example 23), AZT-3-B:FTED (Example 15), and AZT-3-V:FTED (Example 7). On the other hand, the amino group of FAM is not sufficiently nucleophilic to allow satisfactory reaction with an active ester of a carboxylated AZT analog. As a result, CDI is used to mediate the reaction of FAM with a carboxylated AZT analog.

It should be noted that fluorescein derivatives can be radioactively labeled in order to provide tracers for RIAs.

As was previously discussed regarding immunogens, preparation of a test or coating antigen, for example, for an NIA or EIA, is preferably accomplished by reacting the active ester of a carboxyl analog of AZT with a protein such as apoferritin or RSA.

For example AZT-3-MV (Example 1) is first Prepared, which is then subjected to base catalyzed hydrolysis to produce AZT-3-VA (Example 2), followed by reaction of AZT-3-VA with N-hydroxysuccinimide (NOS) to provide AZT-3-V:NOS (Example 3). AZT-3-V:NOS is then converted to its rabbit serum albumin derivative (Example 8) which is then used as the coating antigen in the assay. This rabbit serum albumin derivative can also be used as the developer antigen in nephelometric inhibition immunoassays.

Test Kits

In addition to the foregoing, the present invention contemplates the provision of diagnostic test kits suitable for being utilized with minimal user preparation in connection with the various assays described above. Such kits can be used for the determination of the presence or absence of AZT in a sample of biological fluid as well as determining the level of AZT in a sample containing AZT. Such kits will generally be a set of optimized reagents comprising the combination of antibodies specific to AZT and tracer capable of reacting with the antibodies to produce a detectable antibody-tracer reaction, whereby the antibodies can be intermixed with a sample of biological fluid to be tested and the tracer, and then subjected to the appropriate technique for indicating the presence of AZT and/or the level of AZT in the sample.

In addition, the diagnostic test kits of this invention may optionally contain a precipitating agent, as described herein, suitable for reducing nonspecific background interference, for example fluorescence, due to the presence of various materials in the sample to be analyzed. The test kit may also be supplied with a buffer, as appropriate for the particular assay to which the kit is directed. The test kit may further be supplied with means for separating the antibody-tracer complex from unbound or free tracer in the case where the kit's assay method is heterogeneous as described herein.

Synthesis of AZT Compounds

To further illustrate the foregoing discussion, representative reactions which can be used in various reaction schemes include the following:

A. Acylation of alcohols with cyclic dicarboxylic anhydrides. For example, succinic anhydride reacts with an alcohol to give the corresponding hemisuccinate. Glutaric anhydride may be used in place of succinic anhydride to obtain the glutardioyl derivative. The reaction is preferably conducted in an aprotic organic solvent. Pyridine and/or dimethylaminopyridine are commonly used as catalysts.

B. The alkylation of cyclic imides using a halogenated reactant, Hal—CH$_2$—R, usually where Hal is bromine.

C. Carbodiimide-mediated dehydrations. Carbodiimides (CDIs) mediate reactions between carboxylic acids and amines resulting in the formation of amides, including peptides. For example, carboxylated analogs of AZT can be condensed with the amino group of various isomers of fluoresceinamine in the presence of 1,3-dicyclohexylcarbodiimide (DCC), or such AZT analogs can be reacted with the free amino groups of proteins in an aqueous environment if a water soluble reagent, such as 1-ethyl-3-(3-dimethylaminopropyl)-carbodiimide hydrochloride, (ECDI) is employed. DCC can also be used to condense carboxylated AZT analogs with N-hydroxysuccinimide for the purpose of preparing active esters useful in the acylation of amines.

D. Acylation of amines by active esters. Active esters derived from carboxylated analogs of AZT and leaving groups such as N-hydroxysuccinimide, react with aliphatic amines, such as a carrier protein, resulting in the elimination of the leaving group and simultaneous formation of an amide (peptide) bond.

E. Base catalysed hydrolysis of alkyl esters to provide a carboxylic acid upon acidification.

F. Hydrazinolysis of phthalimides to provide aminoalkyl analogs of AZT. By reacting phthalimidoalkyl substituted AZT (prepared for example, by the reaction of AZT and a bromoalkyl phthalimide) with hydrazine hydrate, amino terminal haptens, such as 3-aminopropyl-AZT (Example 28), are provided. These analogs are quite useful for preparing a variety of other AZT derivatives, as will be appreciated by those skilled in the art, due to the reactivity of the $NH_2$ group. For example, such analogs will react with isothiocyanates, active esters, acid halides, or other electrophilic reagents. They can also be reacted with proteins in the presence of carbodiimide and a variety of other reagents.

G. Addition of amines to isothiocyanates. This general reaction is useful for preparing fluorescein, rhodamine and similar conjugates, since the isothiocyanates of those fluorochromes are commercially available. Such labeling reagents may be homogenous compounds or isomeric mixtures.

H. Iodination of phenols. Electrophilic iodine ($I_2$) attaches itself to phenols in the 2, 4, or 6 position (relative to the phenolic hydroxyl group) unless these positions are blocked by other substituents. This reaction is useful for radioiodinating some haptens to produce radioactive derivatives for use in radioimmunoassays. The iodine can be purchased from commercial sources as nonvolatile Na—($^{125}$I) or Na—($^{131}$I) which is mixed with the phenol to be radioiodinated. An oxidizing agent, e.g. chloramine-T, is then used to convert the iodide to iodize ($I_2$) which then attaches to the aromatic ring. Traditionally, tyrosine methyl ester (TME) analogs are used for iodination. While such analogs can be made from AZT, they have poor solubility in the aqueous solutions encountered during iodinations. As a result the yield of soluble iodinated derivatives will be low. Accordingly, while the yield is sufficient to make an iodinated AZT-R:TME derivative feasible, it is preferred to iodinate an analog of AZT which has greater aqueous solubility, such as a glycine-tyrosine analog or a p-hydroxyphenyl-propionamidoalkyl analog.

I. Nucleophilic aromatic substitution. Alkylamines displace halide from suitably activated, halogenated aromatic or heterocyclic systems.

Representative reaction schemes for the preparation of analogs, immunogens and tracers of this invention are outlined below. For convenience, the representation AZT is used instead of commonly used chemical nomenclature.

A representative reaction scheme for introducing carboxy terminal substituents into the 3 position of AZT is as follows:

1. AZT is reacted with methyl-5-bromovalerate (Reaction B) to provide 5-(3'-azido-3'-deoxythymid-3-yl)-valeric acid methyl ester (AZT-3-MV) (Example 1).

2. The product from step 1 is hydrolysed (Reaction E) to provide 5-(3'-azido-3'-deoxythymid-3-yl)-valeric acid (AZT-3-VA) (Example 2).

3. The product of step 2 is reacted with NOS (Reaction C) to provide N-[5-(3'-azido-3'-deoxythymid-3-yl)-valeryloxy]-succinimide (AZT-3-V:NOS) (Example 3).

4. The product of step 3 is reacted with FTED (Reaction D) to provide the labeled reagent 5-[[5-(3'-azido-3'-deoxythymid-3-yl)-valeramido]-ethylthiocarbamyl]-fluorescein (AZT-3-V:FTED) (Example 7).

As an alternative, the product of step 2 can be reacted with fluoresceinamine (FAM) (Reaction C) to provide the reagent 5-[5-(3'-azido-3'-deoxythymid-3-yl)-valeramido]fluorescein (AZT-3-V:FAM) (Example 6). Also, it is contemplated that the product of step 3 can be reacted with TME (Reaction D) to provide 2-[5-(3'-azido-3'-deoxythymid-3-Yl)-valeramido]-3-(4-hydroxyphenyl)-propionic acid methyl ester (AZT-3-V:TME) which in turn could be reacted with $^{125}$I (Reaction H) to provide the tracer 2-[5-(3'-azido-3'-deoxythymid-3-yl)-valeramido]3-(4-hydroxy-3,5-[$^{125}$I] diiodophenyl)-propionic acid methyl ester or 2-[5-(3'-azido-3'-deoxythymid-3-yl)-valeramido]-3-(4-hydroxy-3,5-[$^{125}$I] diiodophenyl)-propionic acid methyl ester or mixture of the two (AZT-3-V:TME-[$^{125}$I]$_n$), where n is 1 or 2.

Furthermore, the product of step 3 can be used to prepare any number of immunogens using Reaction D as, for example, by reaction with keyhole limpet hemocyanin (KLH) or bovine serum albumin (BSA). In addition, the product of step 3 can be reacted with the enzyme, horseradish peroxidase (HRPO), using Reaction D, to prepare an enzyme labeled derivative of AZT that can be used as a tracer in an enzyme immunoassay. Also, the product of step 3 can be reacted with rabbit serum albumin (RSA) using Reaction D, to provide a test antigen for detecting AZT antibodies, as a coating antigen, or as a developer antigen for an NIA.

Similarly, other 3 position analogs, e.g., butyryl or acetyl analogs, immunogens and derivatives of AZT can be prepared by similar reaction schemes to that described above for AZT-3-valeryl compounds. For example, ethyl-4-bromobutyrate or bromoacetic acid could be used instead of methyl-5-bromovalerate.

If aminoalkyl analogs and derivatives are desired, a suitable reaction scheme is as follows:

1. AZT is reacted with N-(2-bromoethyl)-phthalimide (Reaction B) to provide 3-(2-phthalimidoethyl)-3'-azido-3'-deoxythymidine (3-PHT-E-AZT) (Example 25).

2. The product from step 1 is then subjected to hydrazinolysis (Reaction F) to provide 3-(2-aminoethyl)-3'-azido-3'-deoxythymidine (3-AE-AZT) (Example 27).

3. Alternatively, the product of step 2 is reacted with fluorescein isothiocyanate (FITC) (Reaction G) to provide 5-[2-(3'-azido-3'-deoxythymid-3-yl)-ethylthiocarbamyl]-fluorescein (3-AE-AZT:FITC) (Example 29). Similarly, the product of step 2 can be reacted with erythrosin isothiocyanate (EITC).

The product of step 2 also can be reacted with 3-(p-hydroxyphenyl)propionic acid N-hydroxysuccinimide ester (Reaction D) to prepare 3-[2-[3-(4-hydroxyphenyl)-propionamido]-ethyl]-3'-azido-3'-deoxythymidine (3-AE-AZT:HPPA) (Example 33), which it is contemplated can in turn be converted to the radioactive tracer 3-[2-[3-(4-hydroxy-3-[$^{125}$I] iodophenyl)propionamido]-ethyl]-3'-azido-3'-deoxythymidine or 3-[2-[3-(4-hydroxy-3,5-[$^{125}$I] diiodophenyl)-propionamido]ethyl]-3'-azido-3'-deoxythymidine or mixture of the two (3-AE-AZT:HPP-[$^{125}$I]$_n$), where n is 1 or 2, by reaction with $^{125}$I (Reaction H). Alternatively, it is contemplated that the product of step 2 can be directly iodinated by reaction with the iodinated active ester (N-succinimidyl-3-(4-hydroxy-3-[$^{125}$I] iodophenyl)-propionate, or N-succinimidyl-3-(4-hydroxy-3,5-[$^{125}$I] diiodophenyl)-propionate or a mixture thereof using Reaction D to provide the same compounds mentioned above. Besides preparing iodinated tracers from AZT analogs having a phenolic group, other compounds can also be prepared from the product of step 2 as, for example, by reaction with carboxylated imidazoles using Reaction C.

For preparing 5' position analogs and derivatives the following reaction schemes can be used.

1. AZT is acylated with succinic anhydride to provide 3'-azido-3'-deoxythymidyl-5'-hemisuccinate (AZT-5'-HS) (Example 37). (Reaction A).

2. The product from step 1 is reacted with N-hydroxysuccinimide (NOS) to provide N-[(3'-azido-3-deoxythymid-5'-yl)-succinyloxy]-succinimide (AZT-5'-S:NOS) (Example 38). (Reaction C).

3. The product from step 2 is reacted with tyrosine methyl ester (TME) to provide 2-[(3'-azido-3'-deoxythymid-5'-yl)-succinamido]-3-(4-hydroxyphenyl)-propionic acid methyl ester (AZT-5'-S:TME) (Example 43). (Reaction D).

4. Also, the product from step 3 could be reacted with $^{125}$I to provide the reagent, 2-[(3'-azido-3'-deoxythymid-5'-yl)-succinamido]-3-(4-hydroxy-3-[$^{125}$I] iodophenyl)-propionic acid methyl ester or 2-[(3'-azido-3'-deoxythymid-5'-yl)-succinamido]-3-(4-hydroxy-3,5-[$^{125}$I] diiodophenyl)-propionic acid methyl ester or mixture of the two (AZT-5'-S:TME-[$^{125}$I]$_n$), where n is 1 or 2. (Reaction H).

Alternatively, the product from step 1 can be reacted in the presence of carbodiimide with fluoresceinamine (FAM) (Reaction C) to provide 5-[(3'-azido-3'-deoxythymid-5'-yl)-succinamido]-fluorescein (AZT-5'-S:FAM) (Example 41). An additional alternative is to react the product from step 2 with 5-[N-(2-aminoethyl)-thioureido]fluorescein (fluoresceinthiocarbamylethylenediamine)(FTED) (Reaction D) to provide the tracer 5-[2-(3'-azido-3'-deoxythymid-5'-yl-succinamido)-ethylthiocarbamyl]-fluorescein (AZT-5'-S:FTED) (Example 42).

Furthermore, the product of step 2 can be reacted with bovine serum albumin (Reaction D) to provide an immunogen or reacted with a carrier other than bovine serum albumin such as rabbit serum albumin or horse spleen apoferritin (Reaction D) to provide a test antigen, which in turn can be used to detect haptens or hapten specific antibodies. For example, the test antigen can be used as a coating antigen for enzyme linked immunosorbent assays (ELISA), or as a developer antigen for nephelometric inhibition immunoassays (NIA).

The following nonlimiting examples are provided to further demonstrate to those skilled in the art the preparation of specific AZT analogs, immunogens, antibodies and labeled analogs as well as methods for determining concentration of AZT within the scope of this invention. The quantities indicated for the solvent systems employed in the chromatographic analyses are volume ratios. Thin layer chromatography plates were visualized using short wave UV (254 nm), long wave UV (366 nm), or visible light as appropriate, unless otherwise specified.

EXAMPLE 1

5-(3'-azido-3'-deoxythymid-3-yl)-valeric acid methyl ester (AZT 3-MV)

A solution of 540 mg AZT, 500 ul sodium methoxide solution (4.4M NaOMe in MeOH) and 500 ul of methyl-5-bromovalerate (MBV) in 1 ml N,N'-dimethylpropyleneurea (DMPU) was stirred 1 hour at 70° C. Another 200 ul each of NaOMe solution and MBV were added and the mixture stirred for another hour at 70° C. Then, a further 200 ul each of NaOMe solution (a total of 900 ul NaOMe solution) and 200 ul of MBV (a total of 900 ul MBV) were added and heating at 70° C. was continued for another hour (total heating time of three hours). Analytical thin layer chromatography (TLC) on silica gel-F 250 um using the solvent system CHCl$_3$/MeOH/HOAc (95+5+0.5) showed no AZT remained in the reaction mixture. The mixture was diluted with 20 ml cold water, acidified with HOAc, extracted into EtOAc, concentrated to a small volume under reduced pressure at 45° C. and chromatographed by preparative TLC on silica gel-F 2000 um using the solvent system CHCl$_3$/MeOH/HOAc (95+5+0.5). The band containing the product (R$_f$=0.4) was eluted with MeOH and concentrated to an oil at 45° C. under reduced pressure. The product was homogeneous on analytical TLC.

EXAMPLE 2

5-(3'-azido-3'-deoxythymid-3-yl)-valeric acid (AZT-3-VA)

About 600 mg of the ester AZT-3-MV (Example 1) was dissolved in 5 ml MeOH and then 3 ml of 1N NaOH was added. The mixture was stirred at 60° C. for 30 minutes, then acidified with HOAc and diluted with 25 ml of saturated aqueous NaCl solution. The milky suspension was extracted with EtOAc (5×10 ml) which was concentrated under reduced pressure at 45° C. and chromatographed by preparative TLC on silica gel-F 1000 um using the solvent system CHCl$_3$/MeOH/HOAc (92.5+7.5+0.5). The major band (R$_f$=0.4) was eluted with MeOH and the solvent evaporated under reduced pressure at 45° C. Trituration of the residue with THF gave a pale yellow solid which was stored overnight in vacuo over NaOH pellets. The product was homogeneous on TLC. Its IR spectrum showed a sharp peak at 2100 cm$^{-1}$ indicating the presence of an azido group and also showed a broad peak between 3400–3200 cm$^{-1}$ indicating the presence of a carboxyl group. The UV spectrum (220–320 nm) resembled that of 3-methyl thymidine (prepared by reacting thymidine with diazomethane) which had an absorbance maximum at 268 nm with a molar absorptivity of 8630 and an absorbance minimum at 238 nm with a molar absorptivity of 2700. Based on this similarity, the extinction coefficient for the product was calculated to be E$_{280}^M$=6100. All UV spectra were taken in 0.1M Na-PO$_4$/0.15M NaCl/pH 7.4.

EXAMPLE 3

N-[5-(3'-azido-3'-deoxythymid-3-yl)-valeryloxy]-succinimide (AZT-3-V:MOS)

A suspension of 200 mg AZT-3-VA (Example 2) and 80 mg N-hydroxysuccinimide (NOS) in 5 ml tetrahydrofuran (THF) was chilled on an ice-MeOH bath, followed by addition of 1 ml 1,3-dicyclohexylcarbodiimide (DCC, 1M in THF). The mixture was stirred 90 minutes while the bath temperature rose from −12° C. to +15° C., then the mixture was stirred at room temperature for two hours. Analytical TLC on silica gel-F 250 um using the solvent system CHCl$_3$/MeOH/HOAc (95+5+0.5) showed approximately 80% conversion to the active ester with no byproducts. Therefore, the concentration of AZT-3-V:NOS would be approximately 70 umoles/ml.

EXAMPLE 4

AZT-3-valeryl:BSA (AZT-3-V:BSA)

A solution of 100 mg bovine serum albumin (BSA) in 25 ml deionized water was chilled on an ice bath and approximately 200 umoles of AZT-3-V:NOS (Example 3) was added. Stirring on the ice bath was continued while maintaining the pH between 8.0 and 8.5 by adding 5% $K_2CO_3$ until stable (about 2 hours). Stirring an additional 30 minutes at room temperature gave a slightly turbid solution which was clarified by centrifugation and chromatographed over Sephadex ®G-25 (2.5×50 cm bed), equilibrated and eluted with PBS (0.01M $NaPO_4$/0.15M NaCl/pH 7.4). The protein peak (37 ml, 2.17 mg/ml by biuret) was diluted with PBS to a biuret value of 1 mg/ml stored at −20° C. in 2 ml aliquots. An aliquot of the above, rechromatographed over G-25 had a molar incorporation of 29 moles hapten/66,000 g protein, which did not change after a third passage through G-25. Sephadex is a registered trademark of Pharmacia Fine Chemicals, Inc.

EXAMPLE 5

AZT-3-valeryl:keyhole limpet hemocyanin (AZT 3-V:KLH)

Keyhole limpet hemocyanin (KLH), 130 mg, was allowed to stand overnight in 30 ml deionized water with occasional stirring, then filtered through glass wool. The filtrate which contained about 123 mg protein (biuret) was chilled on an ice bath and treated with approximately 200 umoles AZT-3-V:NOS (Example 3). The mixture was stirred on the ice bath while adding 5% $K_2CO_3$ to maintain the pH between 8.0 and 8.5 until stable (about 2 hours). Three ml of 5% $NaHCO_3$ was added and the pH adjusted with 5% $K_2CO_3$ to 8.4. The suspension was incubated for 24 hours at 4° C. then dialyzed overnight versus cold running deionized water. A small amount of insoluble matter settled out and was removed by decantation. The turbid, but homogeneous supernatant was diluted with deionized water to a biuret value of 1 mg/ml and was stored at −20° C. in 2 ml aliquots.

EXAMPLE 6

5-[5-(3'-azido-3'-deoxythymid-3-yl)-valeramido]-fluorescein (AZT-3-V:FAM)

A solution of 10 mg AZT-3-VA (Example 2), 10 mg fluoresceinamine Isomer I (FAM) and 1.5 ul concentrated HCl in 2.5 ml acetone was treated with 50 umoles DCC and stirred 30 minutes at room temperature. Unless otherwise noted, FAM will refer to Isomer I. It is contemplated that fluoresceinamine Isomer I, Isomer II or an isomeric mixture could be used. An aliquot of the reaction mixture was chromatographed by TLC on silica gel-F 250 um using the solvent system $CHCl_3$/MeOH/HOAc (90+10+1). The major band ($R_f$=0.28) containing Product and FAM was scraped, eluted with MeOH and rechromatographed on $C_{18}$ reversed phase plate containing fluorescent indicator (RPF) 250 um using the solvent system MeOH/$H_2O$/HOAc (50+50+3). The product migrated as a fluorescent band ($R_f$=0.37) while AZT-3-VA and free FAM migrated close to the solvent front. The product was immunologically active by FPIA for AZT and its binding characteristics did not change on repeated chromatography in a reversed phase system.

EXAMPLE 7

5-[5-(3'-azido-3'-deoxythymid-3-yl)-valeramido]-ethyl-thiocarbamyl]-fluorescein (AZT-3-V:FTED)

A solution of 10 mg fluoresceinthiocarbamylethylenediamine (FTED) in 1 ml N,N-dimethylacetamide (DMA) was chilled on an ice bath and treated with approximately 14 umoles of AZT-3-V:NOS (Example 3). The solution was stirred 15 minutes on the ice bath, then three hours at room temperature. The mixture was diluted with 10 ml deionized water and acidified with HCl to precipitate the crude product which was partially purified by preparative TLC on silica gel-F 250 um using the solvent system $CHCl_3$/MeOH/HOAc (80+20+1). The fluorescent band migrating at $R_f$=0.6 was scraped, eluted with MeOH and rechromatographed on RPF 250 um using the solvent system MeOH/$H_2O$/HOAc (33+66+2).

EXAMPLE 8

AZT-3-valeryl:RSA (AZT-3-V:RSA)

A solution of 100 mg rabbit serum albumin (RSA) and 150 mg $NaHCO_3$ in 15 ml deionized water was treated with approximately 35 umoles AZT-3-V:NOS (Example 3) after chilling on an ice bath. The pH was adjusted to 8.5 with 5% $K_2CO_3$ and the mixture incubated overnight at 4° C. The mixture was filtered through a 1.2 um membrane and chromatographed over Sephadex ®G-25 (2.5×50 cm bed), eluting with 0.01M $NaPO_4$/0.15M NaCl/pH 7.4/0.1% $NaN_3$. The protein peak gave a biuret value of 2.53 mg/ml and $A_{280}$=7.455. The calculated molar incorporation (MI) was 27 moles hapten per 66,000 g protein, assuming $E_{280}$=0.61/mg/ml for RSA and $E_{280}{}^M$=5800 for the hapten. The antigen was filtered through a 0.2 um filter and stored at 4° C.

EXAMPLE 9

AZT-3-valeryl:horseradish peroxidase (AZT-3-V:HRPO)

A solution of 15 mg (40 umoles) of AZT-3-VA (Example 2), 10 mg NOS (87 umoles) and 10 mg DCC (50 umoles) in 200 ul of dry DMA was stirred two hours at room temperature. At this point analytical TLC using silica gel-F 250 um and a solvent system of $CHCl_3$/MeOH/HOAc (95+5+0.5) showed about 40% conversion to the active ester. The reaction mixture was added to a solution of 13 mg horseradish peroxidase dissolved in 2 ml of 0.15M borax-HCl, pH 8.5 which was prechilled on an ice bath. The mixture was stirred 30 minutes on the ice bath, then filtered through a 0.45 um polytetrafluorethylene (PTFE) membrane to remove dicyclohexylurea. The clear filtrate was chromatographed over a 1×30 cm column of Sephadex ®G-25, eluting with PBS (0.01M $NaPO_4$/0.15M NaCl/pH 7.4). The protein peak was filtered through a 0.2 um membrane and the clear filtrate stored at −20° C. The preparation was found to have peroxidase activity in a qualitative color reaction and was an active inhibitor in a FPIA for AZT. It was later found to perform satisfactorily as an EIA tracer.

EXAMPLE 10

4-(3'-azido-3'-deoxythymid-3-yl)-butyric acid ethyl ester (AZT-3-EB)

A mixture of 550 mg AZT, 500 ul ethyl-4-bromobutyrate, 500 ul sodium methoxide solution (4.4M NaOMe in MeOH) and 1 ml DMPU was stirred at 60° C. for one hour, then another 200 ul ethyl-4-bromobutyrate and 200 ul NaOMe solution was added and heated another hour at 60° C. The addition of another 200 ul base and 200 ul bromoester followed by heating another hour at 60° C. (total of 3 hours) consumed the last of the AZT as confirmed by TLC. The mixture was diluted with 15 ml deionized water, acidified with 1N HCl to pH 3 and extracted into EtOAc. The organic layer was washed with saturated NaCl solution and evaporated under reduced pressure at 45° C. The product was homogeneous on TLC (silica gel-F 250 um, $CHCl_3$/MeOH (95+5)) and its UV spectrum resembled those of AZT-3-MV (Example 1), AZT-3-VA (Example 2) and 3-methylthymidine which was prepared by reacting thymidine with diazomethane.

EXAMPLE 11

4-(3'-azido-3'-deoxythymid-3-yl)-butyric acid (AZT-3-BA)

Six ml of 1N NaOH was added to 1.5 mmoles of AZT-3-EB (Example 10) in 10 ml of MeOH. The solution was stirred for 1 hour at 60° C., acidified with 1N HCl to pH 3 and diluted with 40 ml of saturated NaCl solution. The crude product was extracted into EtOAc, concentrated and chromatographed by preparative TLC on silica gel-F 2000 um using the solvent system $CHCl_3$/MeOH/HOAc (90+10+1). The band containing the purified product ($R_f$=0.32) was scraped, eluted with MeOH and concentrated to an oil which was stored in vacuo over NaOH pellets. The product was homogeneous by analytical TLC on silica gel-F 250 um using the same solvent system described above and its UV spectrum resembled that of other 3-alkylated azidothymidines.

EXAMPLE 12

N-[4-(3'-azido-3'-deoxythymid-3-yl)-butyrylox]-succinimide. (AZT-3-B:NOS)

A mixture of 10 mg AZT-3-BA (Example 11), 5 mg NOS and 10 mg DCC in 100 ul DMPU was stirred one hour at room temperature.

EXAMPLE 13

5-4-(3'-azido-3'-deoxythymid-3-yl)-butyramido]-fluorescein (AZT-3-B:FAM Isomer I)

A solution of 10 mg AZT-3-BA (Example 11), 10 mg FAM Isomer I, 10 mg DCC, 1.5 ul of concentrated HCl and 2.5 ml of acetone was stirred 5 minutes at 0° C., then 40 minutes at room temperature. The solution was chromatographed by preparative TLC on silica gel-F 1000 um using the solvent system $CHCl_3$/MeOH/HOAc (85+15+1). The major band ($R_f$=0.4) containing product and FAM was scraped and eluted with MeOH, then rechromatographed on RPF 250 um using the solvent system MeOH/$H_2O$/HOAc (40+60+3). In the latter system the conjugate migrated as a band ($R_f$=0.23) which was well separated from FAM and a fluorescent, immunologically inactive component, comigrating at $R_f$=0.63.

EXAMPLE 14

6-[4-(3'-azido-3'-deoxythymid-3-yl)-butyramido]-fluorescein (AZT-3-B:FAM Isomer II)

A solution of 10 mg AZT-3-BA (Example 11), 10 mg FAM Isomer II, 10 mg DCC and 1.5 ul concentrated HCl in 2.5 ml acetone was stirred 5 minutes at 0° C., then 40 minutes at room temperature and chromatographed by preparative TLC on silica gel-F 1000 um using the solvent system $CHCl_3$/MeOH/HOAc (85+15+1). The product·($R_f$=0.5) migrated as a band with a green fluorescence just above the band corresponding to FAM Isomer II ($R_f$=0.43). A control (AZT-3-B:FAM Isomer I; Example 13) had $R_f$=0.46 in this system. The product was eluted with methanol and rechromatographed over RPF 250 um using the solvent system MeOH/$H_2O$/HOAc (40+60+3). In the latter system the conjugate migrated as a band ($R_f$=0.4). For comparison the $R_f$ of AZT-3-B:FAM Isomer I was 0.25.

EXAMPLE 15

5-[[4-(3'-azido-3'-deoxythymid-3-yl)-butyramido]-ethylthiocarbamyl]-fluorescein (AZT 3-B:FTED)

A mixture of 10 mg AZT-3-BA (Example 11), 5 mg NOS and 10 mg DCC in 100 ul DMPU was stirred 1 hour at room temperature. A solution of 10 mg FTED in 100 ul MeOH and 50 ul of 5% $NaHCO_3$ was added and stirred one hour at room temperature during which time 5% $NaHCO_3$ was added in 10 ul aliquots to keep the pH above 7.5. The reaction mixture was diluted with 100 ul of MeOH and a portion chromatographed by TLC on silica gel-F 250 um using the solvent system $CHCl_3$/MeOH/HOAc (85+15+1). The fluorescent band migrating at $R_f$=0.41 was found to contain the active material. The crude product was rechromatographed over RPF 250 um using the solvent system MeOH/$H_2O$/HOAc (33+66+3). The major fluorescent band migrating just above the origin ($R_f$=0.093) was eluted with MeOH. Immunological activity against AZT was confirmed by a fluorescence polarization technique.

EXAMPLE 16

2-4-(3'-azido-3'-deoxythymid-3-yl)-butyramido]-3-(4-hydroxyphenyl)-propionic acid methyl ester (AZT-3-B:TME)

A solution of 25 mg AZT-3-BA (Example 11) and 15 mg NOS in 500 ul THF was chilled on an ice-MeOH bath, 1 ɔ ul of 1M DCC (in THF) was added and the solution was stirred on the bath for 10 minutes, then at room temperature for 3 hours. A solution of 25 mg tyrosine methyl ester (TME) dissolved in 500 ul THF plus 50 ul MeOH was added and the mixture was stirred overnight at room temperature. The suspension was centrifuged to remove dicyclohexylurea and the supernatant was chromatographed by preparative TLC on silica gel-F 1000 um using the solvent system $CHCl_3$/MeOH/HOAc (85+15+1). The major band ($R_f$=0.55) which consisted of product and AZT-3-BA was eluted with MeOH and rechromatographed over RPF 250 um using the solvent system MeOH/$H_2O$/HOAc (33+66+3) where the product ($R_f$=0.32, Pauly positive, ninhydrin negative) was well separated from AZT-3-BA ($R_f$=0.55, Pauly negative, ninhydrin negative). The product was eluted with MeOH. It was found to be immunologically active in a FPIA for AZT.

EXAMPLE 17

3-[2-4-(Fluoresceinyl-5)-6-methoxy-s-triazin-2-yl]aminoethyl]-3'-azido-3'-deoxythymidine (3-AE-AZT:MTAF)

A solution of 10 mg MTAF (Example 31), 10 mg 3-AE-AZT (Example 27) and 2.5 ul triethylamine (Et$_3$N) in 250 ul of THF/MeOH (1+4) was incubated 2.5 hours at 56° C., then 24 hours at room temperature and chromatographed over silica gel-F 250 um using the solvent system CHCl$_3$/MeOH/HOAc (90+10+1), then rechromatographed over RPF 250 um using the solvent system MeOH/H$_2$O/HOAc (50+50+3).

The product was immunologically active in an FPIA for AZT and was homogeneous in the following 3 TLC systems: silica gel-F 250 um using the solvent system CHCl$_3$/MeOH/HOAc (90+10+1) ($R_f$=0.35); RPF 250 um using the solvent system MeOH/H20/15M NH$_4$OH (40+60+3) ($R_f$=0.64); and RPF 250 um using the solvent system MeOH/H$_2$O/HOAc (50+50+3) ($R_f$=0.36).

EXAMPLE 18

N-[4-(3'-azido-3'-deoxythymid-3-yl)-butyryl]-glycyl-L-tyrosine AZT-3-B:Gly-Tyr)

A solution of 50 mg AZT-3-BA (Example 11) and 30 mg NOS in 500 ul DMA at -10° C. was treated with 200 ul DCC (1M in THF) and stirred at −10° C. for 10 minutes, then at room temperature for 3 hours. A solution of 50 mg glycyl-L-tyrosine (Gly-Tyr) and 50 ul of tri-(n-butyl)-amine in 500 ul DMPU was added to the reaction mixture. The suspension was incubated overnight at room temperature, diluted with 10 ml deionized water, acidified to pH 2.5 and extracted into EtOAc. The organic phase was washed with saturated NaCl solution, dried over Na$_2$SO$_4$, concentrated and chromatographed by preparative TLC on silica gel-F 1000 um using the solvent system CHCl$_3$/MeOH/HOAc (75+25+1). The product migrated as a band ($R_f$=0.3) which was Pauly positive and ninhydrin negative. In this system AZT-3-BA ($R_f$=0.78) and NOS ($R_f$=0.65) were both Pauly negative and ninhydrin negative. Reference Gly-Tyr ($R_f$=0.05) was Pauly positive and ninhydrin positive. The band containing the product was eluted with MeOH. It was homogeneous on analytical TLC and its UV spectrum was consistent with the expected structure. It was found to be immunologically active in a fluorescence polarization immunoassay for AZT.

EXAMPLE 19

3-carboxymethyl-3'-azido-3'-deoxythymidine (AZT-3-AA)

A mixture of 560 mg AZT, 15 ml absolute ethanol, 2 ml sodium methoxide solution (4.4M NaOMe in MeOH) and 500 mg bromoacetic acid was refluxed for 5.5 hours, then allowed to stand overnight at room temperature. The next morning, 1 ml NaOMe solution was added followed by 300 mg bromoacetic acid and the mixture refluxed for one hour, at which time the reaction was shown to be complete by TLC on silica gel-F 250 um using the solvent system CHCl$_3$/MeOH/HOAc (85+15+1). The reaction mixture was diluted with five volumes of deionized water and extracted with CHCl$_3$. The aqueous phase was acidified with 1N HCl, and extracted into EtOAc. The EtOAc extract was concentrated under reduced pressure and chromatographed by preparative TLC on silica gel-F 1000 um using the solvent system CHCl$_3$/MeOH/HOAc (85+15+1). The product band ($R_f$=0.25) was scraped, eluted with MeOH and concentrated to a syrup which was flashed repeatedly with CHCl$_3$, MeCl$_2$ and THF until the odor of HOAc was no longer detectable. The oil was stored in vacuo over sodium hydroxide pellets. The product was homogeneous on TLC and its UV spectrum resembled that of AZT-3-VA (Example 2) and 3-methylthymidine. The product was subsequently shown to have immunological activity with antisera to AZT by FPIA.

EXAMPLE 20

N-[2-(3'-azido-3'-deoxythymid-3-yl)-acetoxy]-succinimide (AZT-3-A:NOS)

A mixture of 16 mg AZT-3-AA (Example 19), 8 mg NOS and 10 mg DCC in 2 ml of THF was incubated overnight at room temperature.

EXAMPLE 21

3-carbethoxy-3'-azido-3'-deoxythymidine (AZT-3-A-OEt)

A solution of 267 mg AZT in 1 ml DMPU was treated with 500 ul of sodium methoxide solution (4.4M NaOMe, in MeOH) and 250 ul of ethyl bromoacetate and stirred 30 minutes at room temperature. Another 500 ul NaOMe solution and 250 ul ethyl bromoacetate were added and the mixture was heated 1 hour at 60° C. in a water bath. The resulting suspension was diluted with 15 ml deionized water and extracted with EtOAc. The organic phase was washed, first with 5% NaHCO$_3$ then saturated NaCl solution, concentrated under reduced pressure and chromatographed by preparative TLC on silica gel-F 2000 um using the solvent system CHCl$_3$/MeOH/HOAc (95+5+0.5). Three bands were visualized with UV (254 nm) and were eluted separately with MeOH. Fraction A ($R_f$=0.19) was identified as AZT by TLC and UV spectrum by comparison with an authentic AZT reference. It was also immunologically active in an AZT assay by FPIA. Fractions P ($R_f$=0.37) and C ($R_f$=0.57) had similar UV spectra, resembling that of 3-methylthymidine. Fraction B was immunologically active (approximately 110% "cross-reactivity" relative to AZT in an AZT assay by FPIA). Fraction C was immunologically inactive. Fraction B was therefore evaporated to dryness and saved.

EXAMPLE 22

5-[2-(3'-azido-3'-deoxythymid-3-yl)-acetamido]-fluorescein (AZT-3-A:FAM)

A mixture of 10 mg AZT-3-AA (Example 19), 10 mg FAM, 10 mg DCC, 1.5 ul concentrated HCl and 2.5 ml acetone was stirred at 0° C. for 5 minutes, followed by 40 minutes at room temperature. The suspension was chromatographed by preparative TLC on silica gel-F 1000 um and developed with the solvent system CHCl$_3$/MeOH/HOAc (85+15+1). The major band ($R_f$=0.41) containing product and FAM was scraped and eluted with MeOH, then rechromatographed on RPF 250 um using the solvent system MeOH/H$_2$O/HOAc (33+66+3). In the latter system the conjugate migrated as a band ($R_f$=0.16) which was well separated from FAM and two minor impurities which migrated as an orange band ($R_f$=0.48). The above procedure gave 0.6 umole of purified material.

EXAMPLE 23

5-[2-(3'-azido-3'-deoxythymid-3-yl)-acetamido]-ethyl-thiocarbamyl]-fluorescein (AZT-3-A:FTED)

A mixture of 16 mg AZT-3-AA (Example 19), 8 mg NOS and 10 mg DCC in 2 ml of THF was incubated overnight at room temperature, then added to a solution of 20 mg FTED in 2 ml DMA. The mixture was stirred at room temperature for 60 minutes and diluted with 10 ml of CHCl$_3$. The crude product was extracted into 5 ml of 5% NaHCO$_3$, the aqueous phase acidified with HOAc and extracted into EtOAc. The organic layer was chromatographed by TLC on silica gel-F 250 um using the solvent system CHCl$_3$/MeOH/HOAc (80+20+1). The major fluorescent band ($R_f$=0.45) was scraped, eluted with MeOH and rechromatographed on RPF 250 um using the solvent system MeOH/H$_2$O/HOAc (33+66+3). The product ($R_f$=0.42) was eluted with MeOH.

EXAMPLE 24

2-[2-(3'-azido-3'-deoxythymid-3-yl)-acetamido]-3-(4-hydroxyphenyl)-propionic acid methyl ester (AZT-3-A:TME)

A mixture of 25 mg AZT-3-AA (Example 19), 15 mg NOS and 15 mg DCC in 1 ml of THF was stirred two hours at room temperature, then a solution of 25 mg TME in 500 ul of THF/MeOH (9+1) was added and the mixture was stirred overnight at room temperature. The suspension was filtered through a PTFE membrane to remove dicyclohexylurea and chromatographed by TLC on silica gel-F 250 um using the solvent system CHCl$_3$/MeOH/HOAc (90+10+1). Three major UV-absorbing bands were located: TME, $R_f$=0.13, ninhydrin positive, Pauly positive, migrates with TME reference; NOS, $R_f$=0.33, ninhydrin negative, Pauly negative, migrates with NOS reference; and product, $R_f$=0.40, ninhydrin negative, Pauly positive. The band corresponding to the product was scraped, eluted with MeOH and rechromatographed on RPF 250 um using the solvent system MeOH/H$_2$O/HOAc (33+66+2) to remove a trace of NOS. In this second chromatography system, $R_f$=0.42 (product) and $R_f$=0.81 (NOS). The product was eluted with MeOH/THF (1+1). A saturated aqueous solution was prepared and filtered through a PTFE membrane and stored at −20° C. The saturated aqueous solution was characterized by a UV wavelength scan and concentration of the solute was calculated to be 47 ug/ml, assuming $EM_{275}^M$=8600. The material was also found to be immunologically active (i.e., was found to inhibit binding) in both nephelometric inhibition and fluorescence polarization immunoassays for AZT.

EXAMPLE 25

3-(2-ohthalimidoethyl)-3'-azido-3'-deoxythymidine (3-PHT-E-AZT)

A solution of 300 mg N-(2-bromoethyl)-phthalimide (BEP) and 274 mg AZT in 1 ml of sieve-dried DMPU was treated with 300 ul of sodium methoxide solution (4.4M NaOMe in MeOH) and heated at 70° C. for one hour. Another 300 ul of NaOMe solution and 175 mg BEP were added and the solution again heated at 70° C. for a total of 3.5 hours. The reaction was followed by analytical TLC on silica gel-F 250 um using a solvent system of CHCl$_3$/MeOH/HOAc (95+5+0.5) and was found to be incomplete. Addition of more NaOMe solution and BEP did not increase the yield of the desired product. Unreacted BEP ($R_f$=0.81) and AZT ($R_f$=0.2) were identified using reference markers and by their UV spectra. The product ($R_f$=0.4) and a byproduct ($R_f$=0.62) were differentiated on the basis of their UV spectra and immunological activity. The reaction mixture was acidified with HOAc, diluted with 15 ml deionized water and extracted with EtOAc. The organic phase was washed with saturated NaCl solution, dried over Na$_2$SO$_4$, concentrated under reduced pressure and chromatographed by preparative TLC on silica gel-F 2000 um using the solvent system CHCl$_3$/MeOH/HOAc (96.5+3.3+0.3) and the product eluted with MeOH.

EXAMPLE 26

3-(3-phthalimidopropyl)-3'-azido-3'-deoxythymidine (3-PHT-P-AZT)

A solution of 280 mg AZT, 310 mg N-(3-bromopropyl)-phthalimide (BPP) and 300 ul of sodium methoxide solution (4.4M NaOMe in MeOH) in 1 ml DMPU was heated at 70° C. for one hour, then 145 mg BPP and 300 ul NaOMe solution was added and the mixture heated for another hour at 70° C. Another 175 mg BPP was added and heating was continued for a total of 4 hours at 70° C. The reaction mixture was diluted with 10 volumes deionized water, acidified with 200 ul HOAc and extracted into EtOAc. The organic phase was washed with 5% NaHCO$_3$, deionized water, 0.1M HOAc and saturated NaCl, then concentrated and chromatographed by preparative TLC on silica gel-F 2000 um using the solvent system CHCl$_3$/MeOH/HOAc (96.7+3.3+0.33). The product ($R_f$=0.35) was eluted with MeOH. It was immunologically active in an AZT assay by FPIA.

EXAMPLE 27

3-(2-aminoethyl)-3'-azido-3'-deoxythymidine (3-AE-AZT)

A solution of 100 mg 3-PHT-E-AZT (Example 25) in 1 ml absolute EtOH was treated with 25 ul hydrazine hydrate, incubated overnight at room temperature and chromatographed by preparative TLC on silica gel-F 1000 um using the solvent system CHCl$_3$/MeOH/15M NH$_4$OH (90+10+1). The UV positive band at $R_f$=0.25 was eluted with MeOH. Analytical TLC of the methanol extract in the same solvent system with silica gel-F 250 um showed the product to be homogeneous and ninhydrin positive. In this system a hydrazine reference migrated close to the origin as a UV negative, ninhydrin positive spot and reference phthalhydrazide remained at the origin as a UV positive, ninhydrin negative spot.

EXAMPLE 28

3-(3-aminopropyl)-3'-azido-3'-deoxythymidine (3-AP-AZT)

A solution of approximately 0.5 mmole 3'-PHT-P AZT (Example 26) in methanol was treated with 50 ul hydrazine hydrate and incubated overnight at room temperature. The resulting suspension was filtered through a 0.45 um PTFE membrane and the filtrate chromatographed by preparative TLC on silica gel-F 2000 um using the solvent system CHCl$_3$/MeOH/15M NH$_4$OH (85+15+1). The major band ($R_f$=0.27; UV positive; ninhydrin positive) was well separated from 3-PHT-P-AZT ($R_f=0.78$; UV positive; ninhydrin negative) and from hydrazine ($R_f=0.0$; UV negative; ninhydrin postive). The product was eluted with MeOH. It was found to be immunologically active in an AZT assay by FPIA, was homogeneous on analytical TLC and its UV spectrum resembled that of a 3-alkylated AZT derivative.

EXAMPLE 29

5-[2-(3'-azido-3'-deoxythymid-3-yl)-ethyl-thiocarbamyl]fluorescein (3-AE-AZT:FITC)

A solution of 10 mg 3-AE-AZT (Example 27) in 100 ul MeOH was mixed with a solution of 10 mg fluorescein isothiocyanate (FITC) in 100 ul THF. The mixture was stirred 15 minutes at room temperature, then 2.5 ul $Et_3N$ was added and the dark orange solution was stirred for one hour at room temperature. The mixture was then chromatographed by TLC on silica gel-F 250 um using the solvent system $CHCl_3$/MeOH/HOAc (90+10+1). The free 3-AE-AZT remained close to the origin ($R_f=0.046$) while free FITC migrated faster ($R_f=0.47$) than the major fluorescent band containing the product ($R_f$TM 0.28). The band containing product was eluted with MeOH and rechromatographed over RPF 250 um using the solvent system MeOH/$H_2O$/HOAc (40+60+2) which removed a small amount of fluorescent material from the product ($R_f=0.23$). The product was eluted with MeOH and found to be a satisfactory tracer for determination of AZT by FPIA.

EXAMPLE 30

5-[3-(3'-azido-3'-deoxythymid-3-yl)-propyl-thiocarbamyl]fluorescein (3-AP-AZT:FITC)

A solution of 10 mg 3-AP-AZT (Example 28) in 100 ul MeOH was mixed with a solution of 10 mg FITC in 100 ul THF. The mixture was stirred 15 minutes at room temperature, then 2.5 ul triethylamine ($Et_3N$) was added and the dark orange solution was stirred for 1 hour at room temperature. The mixture was then chromatographed by preparative TLC on silica gel-F 250 um using the solvent system $CHCl_3$/MeOH/HOAc (90+10+1). The free 3-AP-AZT remained close to the origin ($R_f=0.04$) while free FITC ($R_f=0.46$) migrated faster than the product ($R_f=0.29$) which was eluted with MeOH and rechromatographed over RPF 250 um using the solvent system MeOH/$H_2O$/HOAc (40+60+2). The product band ($R_f=0.14$) was eluted with MeOH and subsequently found to be a satisfactory tracer for determination of AZT by FPIA.

EXAMPLE 31

5-[(4-methoxy-6-chloro-s-triazin-2-yl)-amino]-fluorescein (MTAF)

A cold solution of 1.2 g 2,4-dichloro-6-methoxy-s-triazine in 10 ml of acetone was treated with a cold solution of FAM (2 g in 100 ml MeOH), stirred on an ice bath for 3 hours, filtered and washed with acetone, followed by hexane and dried. The orange powder was homogeneous by TLC on silica gel-F 250 um using the solvent system $CHCl_3$/MeOH/HOAc (90+10+1) ($R_f=0.45$).

EXAMPLE 32

3-[3-[4-(fluoresceinyl-5)-6-methoxy-s-triazin-2-yl]aminopropyl]-3'-azido-3'-deoxythymidine (3-AP-AZT:MTAF)

A solution of 10 mg MTAF (Example 31), 10 mg of 3-AP-AZT (Example 28) and 2.5 ul $Et_3N$ in 250 ul MeOH was incubated 90 minutes at 56° C., then 24 hours at room temperature and chromatographed twice over RPF 250 um using the solvent system MeOH/$H_2O$/HOAr: (50+50+3). The product ($R_f=0.25$) was homogeneous on TLC and was found to provide a satisfactory tracer for quantitation of AZT by FPIA.

EXAMPLE 33

3-[2-[3-(4-hydroxyphenyl)-propionamido]-ethyl]-3'-azido-3'-deoxythymidine (3-AE-AZT:HPPA)

A solution of 10 mg 3-(4-hydroxyphenyl)-propionic acid N-hydroxysuccinimide ester (HPP:NOS) in MeOH was mixed with 10 mg of 3-AE-AZT (Example 27) dissolved in 100 ul MeOH. The mixture was stirred 30 minutes at room temperature, followed by addition of 2.5 ul of $Et_3N$. This mixture was incubated overnight at room temperature, and then chromatographed by TLC on silica gel-F 250 um using the solvent system $CHCl_3$/MeOH/HOAc (90+10+1). The following $R_f$ values were observed upon visualization by UV at 254 nm: 3-AE-AZT, 0.034;NOS, 0.28; product, 0.35; HPPA, 0.37; and HPP:NOS, 0.55. The product, unlike 3-(4-hydroxyphenyl)propionic acid (HPPA), was an effective inhibitor of polarization in a FPIA for AZT.

EXAMPLE 34

3-[3-]4-(Fluoresceinyl-5)-6-chloro-s-triazin-2-yl]aminopropyl]-3'-azido-3'-deoxythymidine (3-AP-AZT:DTAF)

A solution of 10 mg dichlorotriazinylaminofluorescein (DTAF), 10 mg 3-AP-AZT (Example 28) and 2.5 ul $Et_3N$ in 250 ul of THF/MeOH (1+4) was incubated 2 hours at 56° C., then chromatographed over silica gel-F 250 um using the solvent system $CHCl_3$/MeOH/HOAc (90+10+1), then rechromatographed over RPF 250 um using the solvent system MeOH/$H_2O$/HOAc (50+50+3).

The product was immunologically active in a FPIA for AZT and was homogeneous in the following 3 TLC systems: silica gel-F 250 um using the solvent system $CHCl_3$/MeOH/HOAc (90+10+1) ($R_f=0.37$); RPF 250 um using the solvent system MeOH/$H_2O$/15M $NH_4OH$ (40+60+3) ($R_f=0.34$); and RPF 250 um using the solvent system MeOH/$H_2O$/HOAc (50+50+3) ($R_f=0.19$).

EXAMPLE 35

6-[2-(3'-azido-3'-deoxythymid-3-yl)-ethyl-thiocarbamyl]erythrosin (3-AE-AZT:EITC)

A solution of 5 mg 3-AE-AZT (Example 27) in 50 ul MeOH was added to a suspension of 10 mg erythrosin isothiocyanate Isomer II (EITC) in 100 ul THF. Unless otherwise noted EITC will refer to Isomer II. It is contemplated that erythrosin isothiocyanate Isomer I, Isomer II or an isomeric mixture could be used. The resulting clear solution was incubated at room temperature for 15 minutes, 2.5 ul $Et_3N$ was added and the clear solution was incubated for 1 hour at room temperature. The reaction mixture was then chromatographed by TLC on silica gel-F 250 um using the solvent system CHCl$_3$/MeOH/HOAc (90+10+1) where the partially purified product (R$_f$=0.07) was eluted with MeOH, then rechromatographed on RPF 250 um using the solvent system MeOH/H$_2$O/15M NH$_4$OH (40+60+3). The major band (R$_f$=0.87) separated from free 3-AE-AZT (R$_f$=0.52) and the purified product was eluted with MeOH. The product showed a maximum absorbance at 534 nm indicating the presence of erythrosin, was immunologically active in an AZT assay by FPIA and was chromatographically homogeneous.

EXAMPLE 36

6-[3-(3'-azido-3'-deoxythymid-3-yl)-propyl-thiocarbamyl]erythrosin (3-AP-AZT:EITC)

A solution of 5 mg 3-AP-AZT (Example 28) in 50 ul MeOH was added to 10 mg EITC in 100 ul THF. The resulting clear solution was incubated 15 minutes at room temperature, 2.5 ul Et$_3$N was added and the clear solution was incubated for another hour at room temperature. This solution was then chromatographed by TLC on silica gel-F 250 um using the solvent system CHCl$_3$/MeOH/HOAc (90+10+1) where the partially purified product (R$_f$=0.076) contaminated with 3-AP-AZT, was eluted with MeOH. The MeOH extract was then rechromatographed by TLC or RPF 250 um using the solvent system MeOH/H$_2$O/15M NH$_4$OH (40+60+3). The major red band (R$_f$=0.66) separated from 3-AP-AZT (R$_f$=0.26) and was eluted with MeOH. The purified material showed the characteristic maximum absorbance at 534 nm indicating erythrosin, was immunologically active in an AZT assay by FPIA, and was chromatographically homogeneous.

EXAMPLE 37

3'-azido-3'-deoxythymidyl-5'-hemisuccinate (AZT-5'-HS)

A mixture of 267 mg AZT, 200 mg succinic anhydride, 200 ul pyridine and 25 mg 4-dimethylaminopyridine (DMAP) in 2 ml THF was stirred for 2 hours at room temperature. The bulk of the pyridine was then removed by coevaporation with CHCl$_3$. The residue was then taken up in 2 ml of MeOH, acidified with 200 ul HOAc and chromatographed by preparative TLC on silica gel-F 1000 um using the solvent system CHCl$_3$/MeOH/HOAc (90+10+0.1). The band containing the product (R$_f$=0.3) was eluted with MeOH. Evaporation of the solvent gave approximately 160 mg (44%) of a pale yellow crystalline solid. The UV spectrum resembled that of AZT. The product was homogeneous in three TLC systems (silica gel-F, alumina-F and reversed phase-F). TLC on alumina readily demonstrated that the material isolated was not AZT. The strong absorption band in its IR spectrum at 2100 cm$^{-1}$ indicated the azido group was intact and the 3465 cm$^{-1}$ band present in the starting material (5'-OH) was missing in the product.

EXAMPLE 38

N-[(3'-azido-3'-deoxythymid-5'-yl)-succinyloxy]-succinimide (AZT-5'-S:NOS)

The active ester was prepared by stirring a mixture of 96.5 mg of AZT-5'-HS (Example 37), 31 mg of NOS and 110 mg of DCC in 3 ml of THF for 2 hours at room temperature. A 75% conversion was estimated by TLC and the mixture was used immediately without isolation of the ester.

EXAMPLE 39

AZT-5'-succinyl:BSA (AZT-5'-S:BSA)

A solution of 30 mg AZT-5'-HS (Example 37) in 2 ml DMA was diluted with 17 ml of 0.15M NaCl and added to 75 mg bovine serum albumin (BSA) dissolved in 25 ml deionized water. Forty mg of dry 1-ethyl-3-(3-dimethylaminopropyl)-carbodiimide hydrochloride (ECDI) was added with rapid stirring, giving a clear solution (pH 5.5) which was stirred overnight at room temperature. The reaction mixture was chromatographed over a column of Sephadex ® G-25 and eluted with PBS (0.01M NaPO$_4$/0.15M NaCl/pH 7.4). The protein peak was diluted with PBS to a biuret value of 1 mg/ml, aliquoted and stored at −20° C. prior to immunization. Molar incorporation was determined from the difference in A$_{280}$ between the conjugate and the protein (calculated from the biuret value) using E$_{280}^M$=44,000 for BSA and E$_{280}^M$=6,500 for the hapten (in PBS). By this method the incorporation was 4.7 moles hapten per 66,000 g protein and did not change on rechromatography.

EXAMPLE 40

AZT-5'-succinyl:BSA (AZT-5'-S:BSA)

A solution of 100 mg BSA in 25 ml deionized water was chilled on an ice bath and adjusted to pH 8.5 with 5% K$_2$CO$_3$. To this BSA solution, approximately 160 umoles of freshly prepared AZT-5'-S:NOS (Example 38) was added with stirring on the ice bath, maintaining pH between 8.0 and 8.5 by addition of more K$_2$CO$_3$ as needed until stable (about 2 hours). The ice bath was then removed and the mixture was stirred an additional 1.5 hours at room temperature and filtered through a 1.2 um membrane to remove dicyclohexylurea. The filtrate was chromatographed over a column of Sephadex ® G-25 (2.5×50 cm) and eluted with PBS (0.01M sodium phosphate (NaPO$_4$)/0.15M NaCl/pH 7.4). The protein peak was diluted with PBS to a biuret value of 1 mg/ml. Molar incorporation was determined from the difference in A$_{280}$ between the conjugate and the protein (calculated from the biuret value) using E$_{280}^M$=44,000 for BSA and E$_{280}^M$=6,500 for the hapten. By this method the moles of hapten or per 66,000 g protein (molar incorporation) equaled 43 and did not change upon rechromatography.

EXAMPLE 41

5-[(3'-azido-3'-deoxythymid-5'-yl)-succinamido]-fluorescein (AZT-5'-S:FAM)

A solution of 10 mg of AZT-5'-HS (Example 37), 10 mg fluoresceinamine (FAM), 1.5 ul concentrated HCl and 10 mg DCC in 2 ml of t-butanol was stirred for 30 minutes at room temperature. An aliquot of the reaction mixture was chromatographed by TLC on silica gel-F 250 um using the solvent system CHCl$_3$/MeOH/HOAc (90+10+1). The product migrated as a band with a greenish fluorescence (R$_f$=0.19) just below the heavy orange band of FAM (R$_f$=0.25). The product band was scraped, eluted with MeOH and rechromatographed on RPF 250 um using the solvent system MeOH/H$_2$O/HOAc (40+60+3). The active product migrated as a fluorescent band (R$_f$=0.26) which was scraped and eluted with MeOH. An orange band (R$_f$0.64) migrated close to the FAM reference ($R_f=0.66$) and AZT-5'-HS moved as a nonfluorescent, UV positive spot ($R_f=0.69$). Immunoactivity of the product was demonstrated by a fluorescence quenching technique for assaying AZT.

EXAMPLE 42

5-[2-(3'-azido-3-'-deoxythymid-5'-yl)-succinamido)-ethylthiocarbamyl]-fluorescein (AZT-5'-S:FTED)

A mixture of 10 mg AZT-5'-HS (Example 37), 5 mg NOS, 10 mg DCC and 100 ul of DMPU was stirred 60 minutes at room temperature. A solution of 10 mg FTED in 100 ul of MeOH and 50 ul of 1N NaOH was added to the reaction mixture and the resulting mixture was stirred 60 minutes at room temperature. During this time, 5% $NaHCO_3$ was added in 10 ul aliquots as needed to maintain the pH above 7.5. The reaction mixture was diluted with 1 ml of MeOH and a portion chromatographed by TLC on silica gel-F 250 um using the solvent system $CHCl_3$/MeOH/HOAc (85+15+1). In this system, the active material ($R_f=0.28$) was located as a fluorescent band migrating between two others ($R_f=0.21$ and $R_f=0.34$). Rechromatography of the active material on RPF 250 um with the solvent system MeOH/$H_2O$/HOAc (33+66+3) left the purified product as a fluorescent band migrating close to the origin. Immunoactivity of this label was demonstrated by FPIA for AZT.

EXAMPLE 43

2-[(3'-azido-3'-deoxythymid-5'-yl)-succinamido]-3-(4-hydroxyphenyl)-propionic acid methyl ester (AZT-5'-S:TME)

A mixture of 25 mg AZT-5'-HS (Example 37), 15 mg NOS and 10 mg DCC in 550 ul THF was stirred for 2 hours at room temperature. A solution of 25 mg TME in 500 ul of THF/MeOH (9+1) was added to the reaction mixture and the resulting mixture stirred at room temperature for 4 hours. The solution was clarified by centrifugation, the supernatant evaporated and the residue taken up in $CHCl_3$, which was washed with 0.5% $NaHCO_3$, then 0.1M HCl. The organic layer was concentrated to a small volume, clarified by adding a small amount of MeOH and chromatographed by TLC on RPF 250 um using the solvent system MeOH/$H_2O$/HOAc (33+66+3). The product ($R_f=0.4$) was scraped and eluted with MeOH/THF (1+1). A 25 ul aliquot of this eluate was diluted with 5 ml deionized water and filtered through a 0.45 um PTFE membrane. A UV wavelength scan showed maximal absorbance at 268 nm, $A_{275}=1.255$; $E_{275}^M=9,900$(calc). Analytical TLC on RPF 250 um using a solvent system of MeOH/$H_2O$/HOAc (33+66+2) showed a homogeneous product ($R_f=0.4$), Pauly positive, ninhydrin negative, which was well separated from AZT-5'-HS ($R_f=0.65$), TME ($R_f=0.80$) and NOS ($R_f=0.86$). The material was immunologically active in AZT assays by NIA and FPIA.

EXAMPLE 44

AZT-5'-succinyl:apoferritin (AZT-5'-S:APO)

A solution of 23 mg horse spleen apoferritin in 5 ml borax-HCl buffer (0.075M, pH 8.5) was chilled on an ice bath and treated with a reaction mixture containing 50 umoles of the freshly prepared AZT-5'-S:NOS (Example 38). The mixture was stirred at 0°-15° C. for 1 hour, then at room temperature for 1 hour and chromatographed over Sephadex ® G-25. Molar incorporation was 8.7 moles of hapten per 66,000 g of protein as determined by $A_{280}$ and biuret. This conjugate was used as the developer antigen for NIA and as a coating antigen for EIA methods for AZT.

EXAMPLE 45

Polyclonal Rabbit Antibodies To AZT

The immunogen (1 mg in 1 ml) was emulsified with an equal volume of Freund's Complete Adjuvant and injected intradermally into each of two female albino rabbits. The process was repeated in two weeks. Two weeks later, monthly subcutaneous booster injections were begun with 0.5 mg in 0.5 ml of the immunogen and 0.5 ml of Freund's Incomplete Adjuvant per animal. The rabbits were bled biweekly by a marginal ear vein technique beginning six weeks after the primary immunization. The blood collected was refrigerated, allowing clots to form, and the supernatant (antiserum) retained. The antiserum from each rabbit was collected and stored, either at $-20°$ C. without preservative, or at 4° C. after addition of sodium azide to a final concentration of 0.1%. The same schedule was followed for each immunogen. Rabbits immunized produced antibodies to AZT.

EXAMPLE 46

Monoclonal antibodies to AZT

Mice were injected with the AZT immunogen AZT-5'-S:BSA (Example 40; immunogen prepared via active ester method). Three injection series were given, each occurring no sooner than 10 days apart. The first two injection series per mouse consisted of subcutaneously injecting 20 ug of immunogen in approximately 40 ul saline emulsified with approximately 160 ul of Freund's Complete Adjuvant and portioned among 6-8 different sites as well as inter-peritoneally (IP) injecting 30 ug of immunogen in approximately 300 ul saline. The third injection series consisted only of subcutaneous injections as described above. No sooner than 10 days after the third injection series and four days prior to fusion, the mice were injected intraveneously with 50 ug immunogen in 200 ul saline. Fusions of immune splenocytes were carried out using SP2/0 mouse myeloma cells. Fused cells were plated into 24 well tissue culture plates in the appropriate selection media. After three weeks, the supernatants were tested for antibody production using AZT-5'-S:APO (Example 44) coated microtiter plates and goat anti-mouse Ig-alkaline phosphatase conjugates. The surviving cells (hybridomas) from wells that contained antibodies to AZT were cloned by limiting dilution into 96-well microtiter plates. After appropriate incubation times, wells were retested for antibodies to AZT and the hybridomas producing such antibodies were recloned.

After monoclonality was established, hybridoma cells were used to induce ascites in mice for large volume production of monoclonal antibodies to AZT. Briefly, 7-30 days prior to induction, mice were injected IP with 0.5 ml 2,6,10,14-tetramethylpentadecane (pristane). After pristane priming, mice were injected with 0.5-1.0 million hybridoma cells in 0.5 ml serum free tissue culture media. Ascites fluid was harvested from the mice 7-30 days later.

EXAMPLE 47

Fluorescence Polarization Immunoassay for AZT

The following procedure illustrates the use of various materials of the invention in a preferred FPIA method.

(1) 50–250 ul AZT sample (standard or unknown) was added per microcentrifuge tube. An equal volume of precipitation reagent was added per microcentrifuge tube. The tubes were centrifuged at greater than 9,000×g for 1 minute.

(2) A 17.5 ul sample of each serum extract was brought to approximately pH 7–8 by the addition of buffer.

(3) 25 ul each of AZT antibodies and AZT tracer were added per tube and the volume per tube brought to approximately 2 ml with buffer.

(4) After an appropriate incubation time, the polarization of each reaction mixture was determined using a polarization spectrofluorimeter.

A plot of polarization versus AZT concentration for a set of AZT standards can be used to determine the concentration of AZT in unknowns by interpolation.

Based on this procedure using antibodies stored at 4° C. with 0.1% sodium azide from Rabbit No. 1 produced in response to immunization with AZT-3-V:BSA which was prepared via active ester (Example 4) as well as using AZT-3-B:FAM Isomer I (Example 13) and AZT standards ranging in concentration from 0.0–14.7 uM, the following data was obtained:

| Sample No. | AZT (uM) | Polarization Units (P × 1000) |
|---|---|---|
| 1 | 0.00 | 166 |
| 2 | 0.2 | 155 |
| 3 | 0.6 | 141 |
| 4 | 1.7 | 118 |
| 5 | 5.0 | 87 |
| 6 | 14.7 | 61 |

EXAMPLE 48

AZT Microtiter Plate Enzyme Immunoassay

To each well of a 96 well microtiter plate was added 100 ul of diluted rabbit antibodies (Example 45) to AZT-3-V:BSA prepared via active ester (Example 4) previously fractionated with ammonium sulfate. After incubation overnight, the plate was washed and 300 ul of diluted normal rabbit serum was added to each well to block any unbound sites on the plastic surface of the microtiter plate. The plate was again washed and the excess moisture removed. Next, 50 ul of AZT sample was added to the appropriate well followed by the addition of 50 ul of AZT-3-V:HRPO (Example 9) to all wells. The plate was incubated for 60 minutes at room temperature. The plate was then washed and 300 ul of diluted o-phenylenediaminehydrogen peroxide substrate solution was added to each well. The color was allowed to develop for 90 minutes at room temperature in the dark. Absorbances were then measured spectrophotometrically for each well. A plot of absorbance versus AZT concentration for a set of AZT standards can be used to determine the concentration of AZT in unknown samples by interpolation. Based on this procedure using antibodies from Rabbit No. 2 produced in response to immunization with AZT-3-V:BSA which was prepared via an active ester (Example 4) and stored at −20° C. without preservative prior to ammonium sulfate fractionation as well as using AZT-3-V:HRPO (Example 9), and AZT standards ranging in concentration from 0.0–101.1 ng/ml, the following data was obtained.

| Sample No. | AZT (ng/ml) | Net Absorbance (B) | % B/Bo |
|---|---|---|---|
| 1 | 0.0 | 0.367 | 100 |
| 2 | 0.1 | 0.323 | 88 |
| 3 | 0.4 | 0.273 | 74 |
| 4 | 1.6 | 0.205 | 56 |
| 5 | 6.3 | 0.149 | 41 |
| 6 | 25.3 | 0.085 | 23 |
| 7 | 101.1 | 0.044 | 12 |

As further illustration of the invention polyclonal antibodies were raised in two rabbits by immunization with the conjugate of Example 4 (AZT-3-V:BSA) as is more fully described in Example 45 and stored at 4° C. with 0.1% sodium azide. A number of tracers were then compared as to their performance in FPIA using the antisera raised from two rabbits. The results of that comparison are set forth in Table 1 below.

TABLE 1

| | | Rabbit 1 | | | Rabbit 2 | | |
|---|---|---|---|---|---|---|---|
| | n | Titer [Ab][1] | Polarization Units (P × 1000) | $ED_{50}$[2] ug/ml AZT | Titer [Ab][1] | Polarization Units (P × 1000) | $ED_{50}$[2] ug/ml AZT |
| A. AZT-$(CH_2)_n$—CO—NH—F* | 1 | 150 | 164 | 1.4 | 105 | 150 | 2.0 |
| | 3 | 450 | 170 | 1.3 | 115 | 179 | 3.9 |
| | 4 | 300 | 179 | 4.0 | 130 | 175 | 8.0 |
| Isomer II | 3 | 150 | 167 | 0.6 | 74 | 159 | 1.4 |
| B. AZT-$(CH_2)_n$—CO—NH—$CH_2$—$CH_2$—NH—CS—NH—F | 1 | 53 | 173 | 2.4 | 28 | 164 | 1.4 |
| | 3 | 200 | 165 | 4.0 | 73 | 184 | 4.0 |
| | 4 | 1 | — | — | 3 | 197 | >>8.0 |
| C. AZT-$(CH_2)_n$—NH—CS—NH—F | 2 | 150 | 180 | 3.9 | 58 | 177 | 2.9 |
| | 3 | 80 | 159 | >4.0 | 80 | 170 | 4.0 |
| D. AZT-$(CH_2)_n$—NH:DTAF | 2 | 250 | 162 | 4.0 | 125 | 156 | >8.0 |
| | 3 | 500 | 171 | 2.0 | 140 | 168 | 4.0 |
| E. AZT-$(CH_2)_n$—NH:MTAF | 2 | 190 | 160 | 2.5 | 100 | 179 | 4.0 |
| | 3 | 550 | 179 | 3.1 | 183 | 170 | ~8.0 |

*F indicates coupling through the 5 position (Isomer I) of fluorescein unless otherwise noted as Isomer II indicating coupling through the 6 position of fluorescein.
[1]TITER was defined as the dilution of antiserum (i.e., [Ab]) required to obtain the given polarization units (P × 1000) with 1 pmole of tracer.
[2]$ED_{50}$ was defined as the concentration of AZT (ug/ml) required to give a 50% reduction in polarization relative to a control (0 tube) containing no unlabeled AZT in a volume of 10 ul.

To summarize for 3 position AZT fluorescent tracers, the order of preference based on the empirical data in Table 1 is as follows:

AZT-3-butyryl:FAM Isomer II
AZT-3-butyryl:FAM Isomer I
AZT-3-acetyl:FAM Isomer I 3-aminopropyl-AZT:DTAF Isomer I
3-aminoethyl-AZT:MTAF Isomer I
AZT-3-acetyl:FTED Isomer I
3-aminopropyl-AZT:MTAF Isomer I AZT-3-B:FAM Isomer I has proved to have satisfactory affinity and sensitivity, however should greater sensitivity and/or affinity be desired, then the more preferred AZT-3-B:FAM Isomer II fluorescent tracer would be utilized.

Although this invention has been described in some detail and by way of various specific examples in order to illustrate the invention, it will be apparent that various equivalents, changes and modifications may be made without departing from the spirit and scope thereof.

What is claimed is:

1. An antibody prepared in response to a compound of the formula:

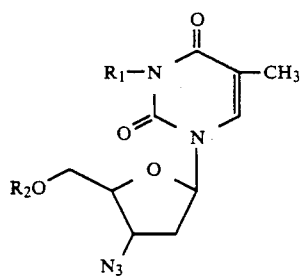

where one of $R_1$ and $R_2$ is hydrogen and the other of $R_1$ and $R_2$ comprises R—Y, R is a linking group, and Y is a carrier.

2. A method for determining AZT in a sample comprising intermixing with said sample a tracer represented by the formula:

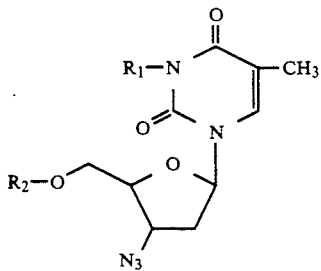

where one of $R_1$ and $R_2$ is hydrogen and the other of $R_1$ and $R_2$ comprises R—X, R is a linking group and X is an indicator moiety, and an antibody capable of specifically recognizing AZT and said tracer, and then determining the amount of tracer bound to antibody as a measure of the amount of AZT in the sample by a suitable assay technique.

3. A method of claim 2 where the indicator moiety is a fluorescent indicator moiety.

4. A method of claim 3 where the fluorescent indicator moiety is fluorescein.

5. A method of any one of claims 2, 3 or 4, where the assay technique is a fluorescence polarization technique.

6. A method of claim 2 where the indicator moiety is an enzyme indicator moiety.

7. A method of claim 6 where the enzyme indicator moiety is horseradish peroxidase or alkaline phosphatase.

8. A method of claim 2 where the assay technique is an enzyme technique.

9. A method for determining AZT in a sample comprising intermixing with said sample a tracer represented by the structure:

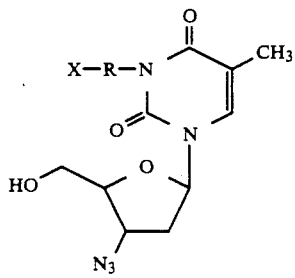

where X is a fluorescent indicator moiety and R is a linking group and an antibody of claim 1, and then determining the amount of tracer bound to antibody by a fluorescence polarization technique as a measure of the amount of AZT in the sample.

10. A diagnostic kit having component parts adapted to be used together to determine the concentration of AZT in a biological fluid comprising:
(a) an antibody of claim 1, and
(b) an indicator represented by the structure:

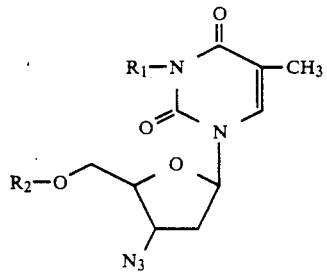

where one of $R_1$ and $R_2$ is hydrogen and the other of $R_1$ $R_2$ comprises R—X, R is a linking group, and X is an indicator moiety capable of binding said antibody.

11. A diagnostic kit of claim 10 where $R_2$ is hydrogen.
12. A diagnostic kit of claim 10 where $R_1$ is hydrogen.
13. A diagnostic kit of claim 11 where the indicator is a fluorescent indicator.
14. A diagnostic kit of claim 12 where the indicator is a fluorescent indicator.
15. A diagnostic kit of claim 10 where the indicator moiety is one represented by the structure:

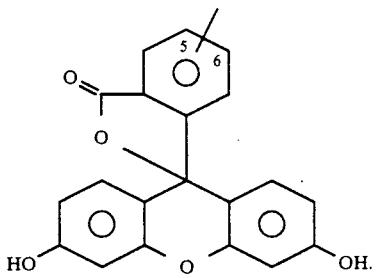

16. A diagnostic kit of claim 10 where the indicator moiety is a fluorescent indicator, further comprising a precipitating agent suitable for reducing non-specific background fluorescence due to materials present in the sample to be analyzed.

17. A hybridoma cell line produced by the method comprising:
(a) immunizing an animal with a compound represented by the structure:

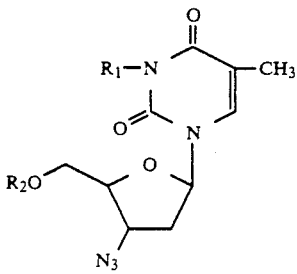

where one of $R_1$ and $R_2$ is hydrogen and the other of $R_1$ and $R_2$ comprises R—Y, R is a linking group and Y is a carrier,
(b) recovering lymphocytes from said immunized animal,
(c) fusing said recovered lymphocytes with a myeloma cell line to produce hybridomas, and
(d) recovering hybridomas that produce antibodies that bind AZT.

18. Monoclonal antibody produced by hybridoma cell lines formed by fusion of cells from a mouse myeloma cell line and spleen cells from a mouse previously immunized with an AZT derivative represented by the structure:

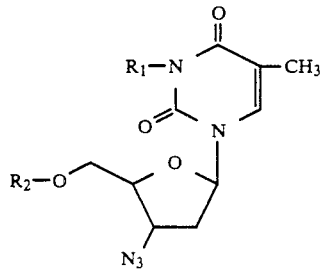

where one of $R_1$ and $R_2$ is hydrogen and the other of $R_1$ and $R_2$ comprises R—Y, R is a linking group and Y is a carrier.

19. An antibody prepared in response to a compound of claim 1 where Y is bovine serum albumin.

20. An antibody prepared in response to a compound of claim 1 where Y is keyhole limpet hemocyanin.

* * * * *